United States Patent
Takeda

(10) Patent No.: US 10,764,506 B2
(45) Date of Patent: Sep. 1, 2020

(54) MEDICAL OBSERVATION DEVICE AND MEDICAL OBSERVATION SYSTEM

(71) Applicant: Sony Olympus Medical Solutions Inc., Tokyo (JP)

(72) Inventor: Takayuki Takeda, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 54 days.

(21) Appl. No.: 16/104,150

(22) Filed: Aug. 17, 2018

(65) Prior Publication Data
US 2019/0075230 A1  Mar. 7, 2019

(30) Foreign Application Priority Data
Sep. 7, 2017 (JP) .................. 2017-171680

(51) Int. Cl.
| | |
|---|---|
| H04N 7/18 | (2006.01) |
| H04N 5/235 | (2006.01) |
| H04N 5/232 | (2006.01) |
| A61B 1/045 | (2006.01) |
| A61B 1/00 | (2006.01) |
| A61B 1/06 | (2006.01) |
| G02B 23/24 | (2006.01) |
| H04N 5/225 | (2006.01) |
| G02B 7/00 | (2006.01) |

(52) U.S. Cl.
CPC ....... *H04N 5/2354* (2013.01); *A61B 1/00006* (2013.01); *A61B 1/00009* (2013.01); *A61B 1/00149* (2013.01); *A61B 1/00188* (2013.01); *A61B 1/045* (2013.01); *A61B 1/06* (2013.01); *A61B 1/0646* (2013.01); *G02B 23/2484* (2013.01); *H04N 5/23296* (2013.01); *H04N 5/232933* (2018.08); *H04N 5/232945* (2018.08); *G02B 7/001* (2013.01); *H04N 2005/2255* (2013.01)

(58) Field of Classification Search
USPC .......................................... 348/69
See application file for complete search history.

(56) References Cited

U.S. PATENT DOCUMENTS

| | | | |
|---|---|---|---|
| 2006/0210262 A1* | 9/2006 | Fujiyoshi ............. | G02B 21/367 396/265 |
| 2018/0081162 A1* | 3/2018 | Abe ..................... | G02B 21/241 |
| 2018/0164538 A1* | 6/2018 | Lee ......................... | G02B 7/09 |
| 2019/0046382 A1* | 2/2019 | Pigazzi .............. | A61G 13/1285 |

FOREIGN PATENT DOCUMENTS

JP   2017-70636   4/2017

* cited by examiner

*Primary Examiner* — Behrooz M Senfi
(74) *Attorney, Agent, or Firm* — Xsensus LLP

(57) ABSTRACT

There is provided a medical observation device including: an imaging control unit configured to control an imaging function of an imaging device. The imaging control unit controls an exposure function of the imaging device on a basis of a detection result of a line of sight of a recognition target so that luminance of a predetermined region in a medical captured image obtained by the imaging device capturing an observation target is changed.

20 Claims, 8 Drawing Sheets

FIG. 5
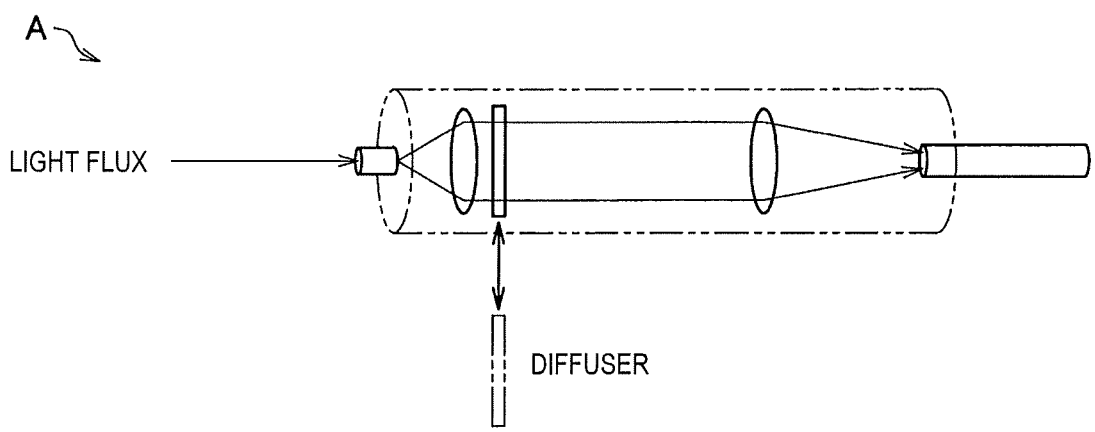
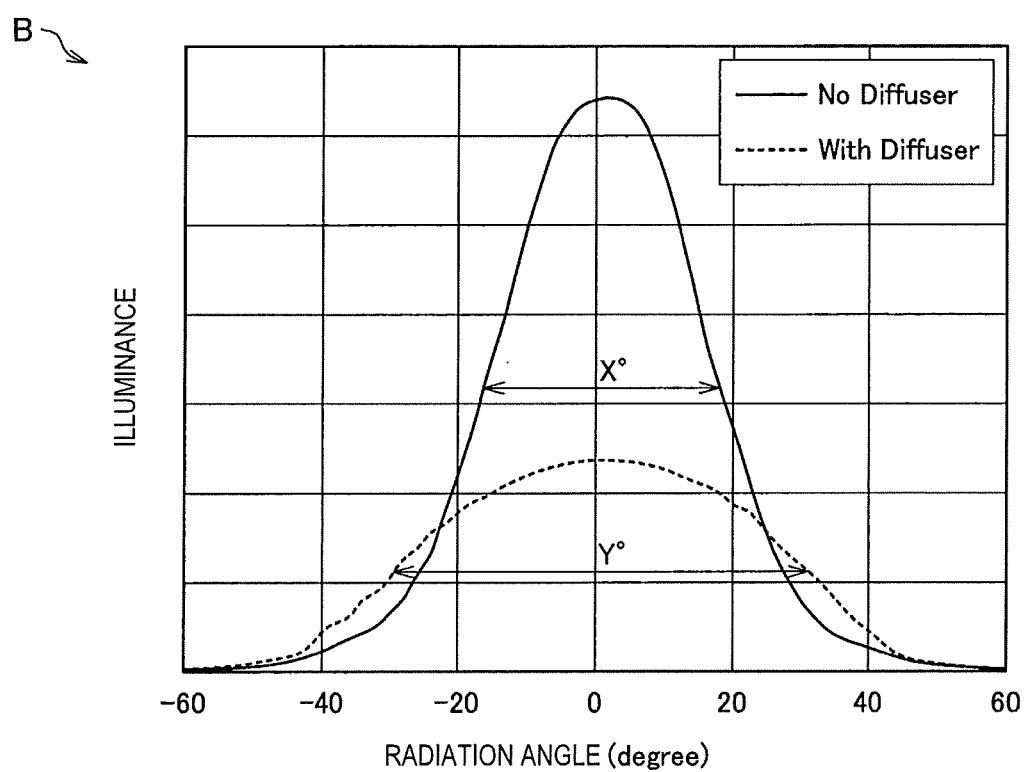

MEDICAL OBSERVATION DEVICE AND MEDICAL OBSERVATION SYSTEM

CROSS REFERENCE TO RELATED APPLICATIONS

This application claims the benefit of Japanese Priority Patent Application JP 2017-171680 filed Sep. 7, 2017, the entire contents of which are incorporated herein by reference.

BACKGROUND

The present disclosure relates to a medical observation device and a medical observation system.

Technologies for controlling surgical devices through a plurality of types of contactless input have been developed. As one of the technologies, for example, the technology disclosed in JP 2017-70636A described below is exemplified.

SUMMARY

In recent years, medical observation devices which enlarge observation targets such as lesions for observation, for example, in order to support microsurgery like neurosurgical operations and to perform endoscopic surgery are used in the medical field. As medical observation devices, for example, medical observation devices with optical microscopes and medical observation devices with imaging devices functioning as electronic imaging-type microscopes are exemplified. Such a medical observation device with an optical microscope will be referred to as an "optical medical observation device" below. In addition, such a medical observation device with an imaging device will be referred to as an "electronic imaging-type medical observation device" or may be referred to simply as a "medical observation device" below. In addition, an image obtained by capturing an observation target using an imaging device included in a medical observation device will be referred to as a "medical captured image" below.

Electronic imaging-type medical observation devices are designed to obtain image quality equal to or higher than that of optical medical observation devices accompanied by high image quality of imaging devices and high resolution of display devices on which captured images are displayed. In addition, it is not necessary for users who use such electronic imaging-type medical observation devices (e.g., medical staff including operators, assistants of operators, etc.) to look into eyepieces of optical microscopes as in cases in which they use optical medical observation devices, and thus the users can move positions of imaging devices more freely. Thus, using electronic imaging-type medical observation devices is advantageous in that microsurgery and the like can be supported more flexibly, and thus use of electronic imaging-type medical observation devices has been progressing in the medical field.

In surgery in which an electronic imaging-type medical observation device is used, an operator performs various kinds of treatments such as a surgical procedure on an operative site in accordance with a surgical technique, for example, while observing the operative site with reference to a medical captured image displayed on a display screen. In addition, in surgery in which a medical observation device is used, there are cases in which the medical observation device is operated by a person other than an operator, for example, a scopist (an endoscope (an example of a medical observation device) operator). Thus, a medical captured image displayed on a display screen may not be an "image in which an operative site that an operator desires to observe can be easily viewed." In addition, in order to make a "medical captured image in which an operative site that an operator desires to observe is easily viewed," a separate operation for making an image having a favorable signal-noise ratio (S/N) by, for example, adjusting intensity of illumination or the like is necessary. Thus, there is concern of convenience of medical staff including operators, assistants of operators, scopists, and the like being impaired in a medical observation system of the related art. In addition, in the medical field, there is a potential need for medical observation devices with higher convenience.

The present disclosure proposes a novel and improved medical observation device and medical observation system that can improve convenience.

According to an embodiment of the present disclosure, there is provided a medical observation device including: an imaging control unit configured to control an imaging function of an imaging device. The imaging control unit controls an exposure function of the imaging device on a basis of a detection result of a line of sight of a recognition target so that luminance of a predetermined region in a medical captured image obtained by the imaging device capturing an observation target is changed.

In addition, according to an embodiment of the present disclosure, there is provided a medical observation system including: a medical observation device including an imaging control unit configured to control an imaging function of an imaging device; and a display device configured to display a medical captured image captured by the imaging device on a display screen. The imaging control unit of the medical observation device controls the exposure function of the imaging device on a basis of a detection result of a line of sight of a recognition target so that luminance of a predetermined region in the medical captured image is changed.

According to an embodiment of the present disclosure, convenience can be improved.

Note that the effects described above are not necessarily limitative. With or in the place of the above effects, there may be achieved any one of the effects described in this specification or other effects that may be grasped from this specification.

BRIEF DESCRIPTION OF THE DRAWINGS

FIG. 5 shows explanatory diagrams for describing a control method according to an embodiment of the present disclosure;

DETAILED DESCRIPTION OF THE EMBODIMENT(S)

Figure 1:
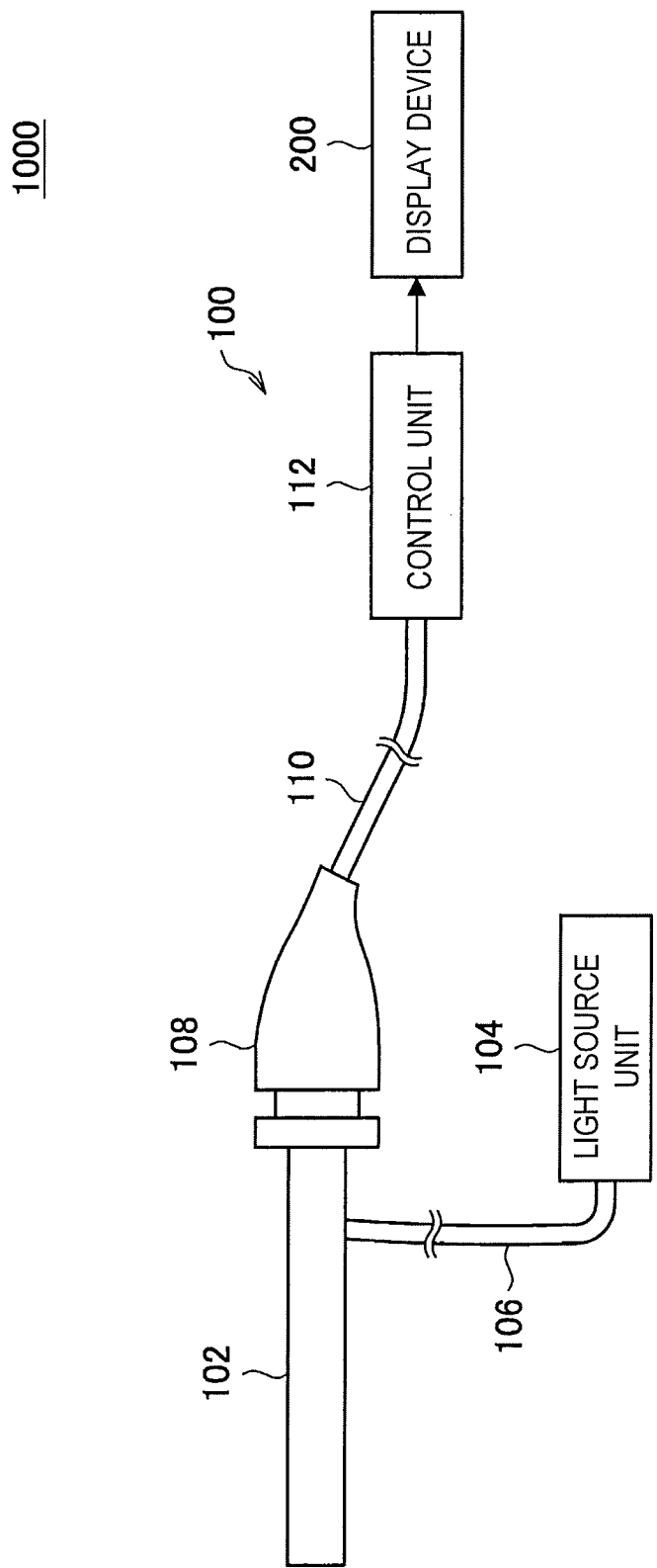
FIG. 1 is an explanatory diagram illustrating a first example of a configuration of a medical observation system according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

In addition, description will be provided below in the following order.
1. Medical observation system according to present embodiment and control method according to present embodiment
2. Program according to present embodiment (Medical Observation System According to Present Embodiment and Control Method According to Present Embodiment)

An example of a medical observation system according to the present embodiment will be described, and then a control method according to the present embodiment that can be applied to the medical observation system according to the present embodiment will be described below.
[1] Configuration of Medical Observation System
[1-1] Medical Observation System According to First Example FIG. 1 is an explanatory diagram illustrating a first example of a configuration of a medical observation system 1000 according to the present embodiment, showing an example of a medical observation system having a medical observation device 100 that functions as an endoscope device that is an example of an electronic imaging-type medical observation device. The medical observation system 1000 illustrated in FIG. 1 has, for example, the medical observation device 100 and a display device 200.

Note that the medical observation system according to the first example is not limited to the example illustrated in FIG. 1.

The medical observation system according to the first example may further have a control device (not illustrated) that controls various operations of the medical observation device 100. An example in which the medical observation device 100 has the function of the control device (not illustrated) in the medical observation system 1000 illustrated in FIG. 1 when the medical observation device 100 has the control unit (which will be described below) that performs a process relating to the control method according to the present embodiment as will be described below is shown.

As the control device (not illustrated), for example, an arbitrary apparatus that can perform the process related to the control method according to the present embodiment such as a "medical controller," or a "computer such as a server" is exemplified. In addition, the control device (not illustrated) may be, for example, an integrated circuit (IC) that can be incorporated into the above-described apparatus.

In addition, the medical observation system according to the first example may have a plurality of medical observation devices 100 and display devices 200. In a case in which a plurality of medical observation devices 100 are provided, each of the medical observation devices 100 performs the process related to the control method of the medical observation device 100 which will be described below. In addition, in the case in which the medical observation system according to the first example has a plurality of medical observation devices 100 and display devices 200, the medical observation devices 100 and the display devices 200 correspond to each other one to one, or the plurality of medical observation devices 100 may correspond to one display device 200. In the case in which the plurality of medical observation devices 100 correspond to one display device 200, for example, a switching operation is performed in the display device 200 to switch images captured by the medical observation devices 100 to be displayed on the display screen.

In addition, the medical observation system according to the first example may also have, for example, a line-of-sight detection sensor that can detect lines of sight. As the line-of-sight detection sensor, for example, a "sensor unit that has a stereo camera and a processor and detects a line of sight from an image captured by the stereo camera" is exemplified. In addition, the line-of-sight detection sensor may be a sensor of an arbitrary type that can detect a line of sight, for example, a "sensor which is provided in a wearable device worn on a head for use, such as an eyewear type device, and detects a line of sight in a corneal reflection method using infrared rays or the like."

In the case in which the medical observation system according to the first example has the line-of-sight detection sensor, the medical observation device 100 can perform the process relating to the control method according to the present embodiment using the detection result of the line-of-sight detection sensor as will be described below. Note that the line-of-sight detection sensor may be an external sensor of the medical observation system according to the first example.

[1-1-1] Display Device 200

The display device 200 is a display section of the medical observation system 1000, and corresponds to an external display device with respect to the medical observation device 100. The display device 200 displays various images, for example, medical captured images (moving images or a plurality of still images; the same applies below) captured by the medical observation device 100, images relating to a user interface, and the like. In addition, the display device 200 may be capable of performing 3D display. Display by the display device 200 is controlled by, for example, the medical observation device 100 or the control device (not illustrated).

The display device 200 of the medical observation system 1000 is installed in an arbitrary place at which the display device can be visually recognized by a person relating to surgery such as an operator within an operating room, for example, a wall surface, a ceiling, a floor of the operating room. As the display device 200, for example, a liquid crystal display, an organic electro-luminescence (EL) display, a cathode ray tube (CRT) display, or the like is exemplified.

Note that the display device 200 is not limited to the above-described example.

The display device 200 may be an arbitrary wearable device worn on the body of an operator or the like for use, for example, a head-mounted display, an eyewear-type device, or the like.

The display device 200 is driven by, for example, power supplied from an internal power supply included in the display device 200 such as a battery, power supplied from a connected external power supply, or the like. An example of a configuration of the display device 200 will be described below.

[1-1-2] Medical Observation Device 100

The medical observation device 100 constituting the medical observation system 1000 according to the first example is an endoscope device. In a case in which the medical observation device 100 illustrated in FIG. 1 is used during surgery, for example, an operator (an example of a user of the medical observation device 100) observes an operative site with reference to a medical captured image captured by the medical observation device 100 and displayed on the display screen of the display device 200, and performs various treatments such as a procedure on the operative site in accordance with a surgical technique.

The medical observation device 100 illustrated in FIG. 1 includes, for example, an insertion member 102, a light source unit 104, a light guide 106, a camera head 108, a cable 110, and a control unit 112. The medical observation device 100 is driven by, for example, power supplied from an internal power supply included in the medical observation device 100 such as a battery, power supplied from a connected external power supply, or the like.

The insertion member 102 has an elongated shape and has an optical system that collects incident light therein. A tip of the insertion member 102 is inserted into, for example, a body cavity of a patient. A rear end of the insertion member 102 is connected to a tip of the camera head 108 to be detachable therefrom. In addition, the insertion member 102 is connected to the light source unit 104 via the light guide 106 and thus receives supply of light from the light source unit 104.

The insertion member 102 may have, for example, a material having no flexibility or of a material having flexibility. The medical observation device 100 can be called a rigid endoscope or a flexible endoscope depending on a material forming the insertion member 102.

The light source unit 104 is connected to the insertion member 102 via the light guide 106. The light source unit 104 supplies light to the insertion member 102 via the light guide 106. In addition, the light source unit 104 is connected by wire or wirelessly to the control unit 112, and light emitted from the light source unit 104 is controlled by the control unit 112.

Light supplied to the insertion member 102 is injected from the tip of the insertion member 102 and radiated to an observation target such as a tissue in a body cavity of a patient. In addition, light reflected from the observation target is collected by the optical system inside the insertion member 102.

The camera head 108 has a function of imaging an observation target. The camera head 108 is connected to the control unit 112 via the cable 110 that is a signal transmission member. The camera head 108 captures the observation target by photoelectrically converting reflected light from the observation target collected by the insertion member 102, and outputs an image signal (a signal indicating a medical captured image) obtained from the imaging to the control unit 112 via the cable 110. Note that an example of a configuration of the camera head 108 will be described below.

In the medical observation device 100 functioning as an endoscope device, for example, the insertion member 102, the light source unit 104, and the camera head 108 play a role of an "imaging device that is inserted into the inside of the body of a patient and images the inside of the body."

The control unit 112 plays a role of performing the process related to the control method according to the present embodiment and controls the imaging function of the imaging device. More specifically, the control unit 112 controls each of the light source unit 104 and the camera head 108.

In addition, the control unit 112 includes a communication device (not illustrated), and transmits an image signal output from the camera head 108 to the display device 200 in arbitrary wireless communication or arbitrary wired communication. The control unit 112 may transmit an image signal and a display control signal to the display device 200.

As the communication device (not illustrated) included in the control unit 112, for example, an IEEE 802.15.1 port and a transmission/reception circuit (wireless communication), an IEEE 802.11 port and a transmission/reception circuit (wireless communication), a communication antenna and an RF circuit (wireless communication), an optical communication device (wired communication or wireless communication), a LAN terminal and a transmission/reception circuit (wired communication), or the like are exemplified. The communication device (not illustrated) may be capable of communicating with one or two or more external devices using a plurality of communication methods.

In addition, the control unit 112 may perform a predetermined process on the image signal output from the camera head 108 and transmit the image signal that has undergone the predetermined process to the display device 200. Examples of the predetermined process with respect to the image signal include one or two or more processes among various kinds of processes including gamma correction, adjustment of white balance, image enlargement or reduction in accordance with an electronic zoom function, and inter-pixel correction.

Note that the control unit 112 may store the medical captured image on the basis of the image signal.

As the control unit 112, for example, a camera control unit (CCU) is exemplified.

The medical observation device 100 functioning as an endoscope device has, for example, a hardware configuration illustrated with reference to FIG. 1. In the medical observation device 100 functioning as an endoscope device, for example, the insertion member 102, the light source unit 104, and the camera head 108 play the role of an imaging device, and the control unit 112 controls imaging of the imaging device.

Note that the medical observation system 1000 according to the present embodiment is not limited to the configuration with the medical observation device 100 functioning as an endoscope device.

[1-2] Medical Observation System According to Second Example

Figure 2:
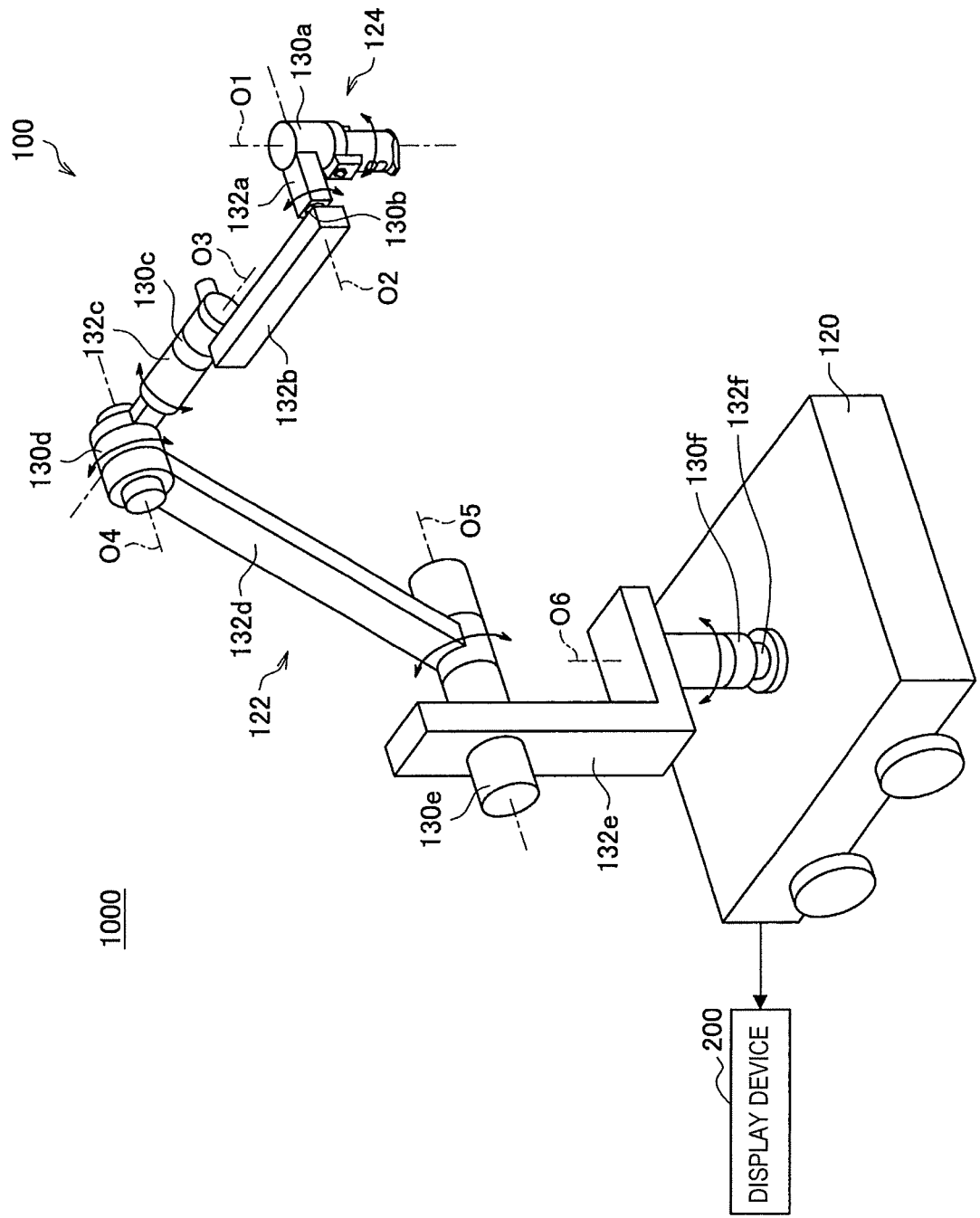
FIG. 2 is an explanatory diagram illustrating a second example of the configuration of the medical observation system according to an embodiment of the present disclosure

FIG. 2 is an explanatory diagram illustrating a second example of the configuration of the medical observation system 1000 according to the present embodiment, showing an example of the medical observation system having a medical observation device 100 functioning as an electronic imaging-type medical observation device according to another example. The medical observation system 1000 illustrated in FIG. 2 has, for example, the medical observation device 100 and a display device 200.

Note that the medical observation system according to the second example is not limited to the example illustrated in FIG. 2.

The medical observation system according to the second example may further have, for example, a control device (not illustrated) that controls various operations of the medical observation device 100, similarly to the medical observation system according to the first example.

In addition, the medical observation system according to the second example may have a plurality of medical observation devices 100 and a plurality of display devices 200, similarly to the medical observation system according to the first example.

In addition, the medical observation system according to the second example may also have a line-of-sight detection sensor, similarly to the medical observation system according to the first example. In the case in which the medical observation system according to the second example has a line-of-sight detection sensor, the medical observation device 100 can perform the process relating to the control method according to the present embodiment using a detection result of the line-of-sight detection sensor as will be described below. Note that the line-of-sight detection sensor may be an external sensor of the medical observation system according to the second example.

[1-2-1] Display Device 200

The display device 200 constituting the medical observation system according to the second example has a similar function and configuration to the display device 200 constituting the medical observation system according to the first example.

[1-2-2] Medical Observation Device 100

The medical observation device 100 constituting the medical observation system 1000 according to the second example is an electronic imaging-type medical observation device according to another example. An example of a hardware configuration of the medical observation device 100 functioning as an electronic imaging-type medical observation device will be described with reference to FIG. 2.

The medical observation device 100 functioning as an electronic imaging-type medical observation device includes, for example, a base 120, an arm 122, and an imaging device 124.

In addition, although not illustrated in FIG. 2, the medical observation device 100 may also include, for example, one or two or more processors (not illustrated) constituted by an arithmetic circuit such as a micro-processing unit (MPU), a read only memory (ROM; not illustrated), a random access memory (RAM; not illustrated), and a recording medium (not illustrated), and a communication device (not illustrated). The medical observation device 100 is driven by, for example, power supplied from an internal power supply included in the medical observation device 100 such as a battery, power supplied from a connected external power supply, or the like.

The processors (not illustrated) function as a control unit which will be described below. The ROM (not illustrated) stores control data such as programs and arithmetic parameters to be used by the processors (not illustrated). The RAM (not illustrated) temporarily stores programs executed by the processors (not illustrated) and the like.

The recording medium (not illustrated) functions as a storage unit. The recording medium (not illustrated) stores, for example, various kinds of data such as data relating to the control method according to the present embodiment and various applications. Here, as the recording medium (not illustrated), for example, a magnetic recording medium such as a hard disk, a non-volatile memory such as a flash memory, or the like is exemplified. In addition, the recording medium (not illustrated) may be detachable from the medical observation device 100.

The communication device (not illustrated) is a communication section included in the medical observation device 100, and plays a role of performing wireless or wired communication with an external device such as the display device 200. Here, as the communication device (not illustrated), for example, an IEEE 802.15.1 port and a transmission/reception circuit, an IEEE 802.11 port and a transmission/reception circuit, a communication antenna and an RF circuit, an optical communication device, a LAN terminal and a transmission/reception circuit, or the like are exemplified. The communication device (not illustrated) may be capable of communicating with one or two or more external devices in a plurality of communication methods.

[1-2-2-1] Base 120

The base 120 is the base of the medical observation device 100, and is connected to one end of the arm 122 to support the arm 122 and the imaging device 124.

In addition, the base 120 has, for example, casters, and the medical observation device 100 stands on the floor via the casters. By having the casters, the medical observation device 100 can be easily moved on the floor with the casters.

[1-2-2-2] Arm 122

The arm 122 is constituted by a plurality of links connected to each other by joints.

In addition, the arm 122 supports the imaging device 124. The imaging device 124 supported by the arm 122 is three-dimensionally movable, and the arm 122 helps the imaging device 124 to maintain a position and a posture after movement.

More specifically, the arm 122 is constituted by, for example, a plurality of joints 130a, 130b, 130c, 130d, 130e, and 130f and a plurality of links 132a, 132b, 132c, 132d, 132e, and 132f that are connected by the joints 130a, 130b, 130c, 130d, 130e, and 130f to revolve. A rotatable range of each of the joints 130a, 130b, 130c, 130d, 130e, and 130f is arbitrarily set in the design stage, the manufacturing stage, or the like so that desired movement of the arm 122 is realized.

That is, in the medical observation device 100 illustrated in FIG. 2, six degrees of freedom with respect to movement of the imaging device 124 are realized by six rotation axes (a first axis O1, a second axis O2, a third axis O3, a fourth axis O4, a fifth axis O5, and a sixth axis O6) corresponding to the six joints 130a, 130b, 130c, 130d, 130e, and 130f constituting the arm 122. More specifically, in the medical observation device 100 illustrated in FIG. 2, movement of six degrees of freedom including three translational degrees of freedom and three rotational degrees of freedom is realized.

Each of the joints 130a, 130b, 130c, 130d, 130e, and 130f has an actuator (not illustrated), and each of the joints 130a, 130b, 130c, 130d, 130e, and 130f rotates at a corresponding rotational axis by driving of the actuator (not illustrated). Driving of the actuator (not illustrated) is controlled by, for example, a processor functioning as a control unit which will be described below or an external control device (not illustrated).

Since each of the joints 130a, 130b, 130c, 130d, 130e, and 130f rotates at a corresponding rotational axis by driving of the actuator (not illustrated), various kinds of operations of the arm 122, for example, stretching, shrinking (folding), and the like of the arm 122, are realized.

The joint 130*a* has a substantially cylindrical shape, and supports the imaging device 124 (an upper end portion of the imaging device 124 in FIG. 2) to be revolvable around a rotation axis (the first axis O1) parallel to a central axis of the imaging device 124 at a tip portion of the joints 130*a* (a lower end part thereof in FIG. 2). Here, the medical observation device 100 is configured such that the first axis O1 matches the optical axis of the imaging device 124. That is, by causing the imaging device 124 to revolve around the first axis O1 illustrated in FIG. 2, a medical captured image captured by the imaging device 124 becomes an image in which a line of sight is changed to rotate.

The link 132*a* is a substantially rod-shaped member, and fixedly supports the joint 130*a*. The link 132*a* extends, for example, in a direction orthogonal to the first axis O1 and is connected to the joint 130*b*.

The joint 130*b* has a substantially cylindrical shape and supports the link 132*a* to be revolvable around the rotation axis (the second axis O2) orthogonal to the first axis O1. In addition, the link 132*b* is fixedly connected to the joint 130*b*.

The link 132*b* is a substantially rod-shaped member and extends in a direction orthogonal to the second axis O2. In addition, the joint 130*b* and the joint 130*c* are respectively connected to the link 132*b*.

The joint 130*c* has a substantially cylindrical shape and supports the link 132*b* to be revolvable around the rotation axis (the third axis O3) orthogonal to the first axis O1 and the second axis O2. In addition, one end of the link 132*c* is fixedly connected to the joint 130*c*.

Here, by causing the tip side of the arm 122 (the side on which the imaging device 124 is provided) to revolve around the second axis O2 and the third axis O3, the imaging device 124 can be moved so that a position of the imaging device 124 is changed within a horizontal plane. That is, since rotation around the second axis O2 and the third axis O3 is controlled in the medical observation device 100, a line of sight of a medical captured image can be moved within a plane.

The link 132*c* has a member having one end in a substantially cylindrical shape and the other end in substantially a rod shape. The one end of the link 132*c* is fixedly connected to the joint 130*c* such that the central axis thereof and the central axis of the substantially cylindrical shape are the same. In addition, the other end of the link 132*c* is connected to the joint 130*d*.

The joint 130*d* has a substantially cylindrical shape and supports the link 132*c* to be revolvable around a rotational axis (the fourth axis O4) orthogonal to the third axis O3. The link 132*d* is fixedly connected to the joint 130*d*.

The link 132*d* is a substantially rod-shaped member and extends to be orthogonal to the fourth axis O4. One end of the link 132*d* is fixedly connected to the joints 130*d* to abut against a side face of the substantially cylindrical shape of the joint 130*d*. In addition, the other end of the link 132*d* (the end on the opposite side to the side on which the joint 130*d* is connected) is connected to the joint 130*e*.

The joint 130*e* has a substantially cylindrical shape and supports one end of the link 132*d* to be revolvable around the rotational axis (the fifth axis O5) parallel to the fourth axis O4. In addition, the joint 130*e* is connected to one end of the link 132*e*.

Here, the fourth axis O4 and the fifth axis O5 are rotational axis that can move the imaging device 124 in the vertical direction. By causing the tip side of the arm 122 (the side on which the imaging device 124 is provided) to revolve around the fourth axis O4 and the fifth axis O5, a position of the imaging device 124 in the vertical direction is changed. Thus, by causing the tip side of the arm 122 (the side on which the imaging device 124 is provided) to revolve around the fourth axis O4 and the fifth axis O5, a distance between the imaging device 124 and an observation target such as an operative site of a patient or the like can be changed.

The link 132*e* is a member constituted by a combination of a first member having a substantially L shape with one side extending in the vertical direction and the other side extending in the horizontal direction and a rod-shaped second member extending vertically downward from a portion of the first member extending in the horizontal direction. A portion of the first member of the link 132*e* extending in the vertical direction is fixedly connected to the joint 130*e*. In addition, the second member of the link 132*e* is connected to the joint 130*f*.

The joint 130*f* has a substantially cylindrical shape and supports the link 132*e* to be revolvable around a rotational axis (the sixth axis O6) parallel to the vertical direction. In addition, the joint 130*f* is fixedly connected to the link 132*f*.

The link 132*f* is a substantially rod-shaped member and extends in the vertical direction. One end of the link 132*f* is connected to the joint 130*f*. In addition, the other end of the link 132*f* (the end on the opposite side to the side on which the joints 130*f* is connected) is fixedly connected to the base 120.

Since the arm 122 has the above-described configuration, six degrees of freedom with respect to movement of the imaging device 124 are realized in the medical observation device 100.

Note that a configuration of the arm 122 is not limited to the above-described example.

For example, a brake that regulates rotation of each of the joints 130*a*, 130*b*, 130*c*, 130*d*, 130*e*, and 130*f* may be provided in each of the joints 130*a*, 130*b*, 130*c*, 130*d*, 130*e*, and 130*f* of the arm 122. As a brake according to the present embodiment, for example, an arbitrary type of brake such as a mechanically driven brake or an electrically driven electromagnetic brake is exemplified.

Driving of the brake is controlled by, for example, a processor that functions as a control unit which will be described below or an external control device (not illustrated). Since driving of the brake is controlled, an operation mode of the arm 122 is set in the medical observation device 100. As operation modes of the arm 122, for example, a fixed mode and a free mode are exemplified.

Here, the fixed mode according to the present embodiment is an operation mode in which, for example, a position and a posture of the imaging device 124 are fixed by a brake regulating rotation at each rotational axis provided in the arm 122. When the arm 122 is the fixed mode, an operation state of the medical observation device 100 is a fixed state in which a position and a posture of the imaging device 124 are fixed.

In addition, the free mode according to the present embodiment is an operation mode in which, when the brake is released, each rotational axis provided in the arm 122 is freely rotatable. In the free mode, for example, a position and a posture of the imaging device 124 can be adjusted through a direct operation by an operator. Here, a direct operation according to the present embodiment means, for example, an operation in which an operator grabs the imaging device 124 with his or her hand and moves the imaging device 124 in person.

[1-2-2-3] Imaging Device 124

The imaging device 124 is supported by the arm 122 and captures an observation target, for example, an operative site of a patient, or the like. Imaging by the imaging device 124 is controlled by, for example, a processor that functions as a control unit, which will be described below, or an external control device (not illustrated).

The imaging device 124 has a configuration corresponding to, for example, an electronic imaging-type microscope.

Figure 3:
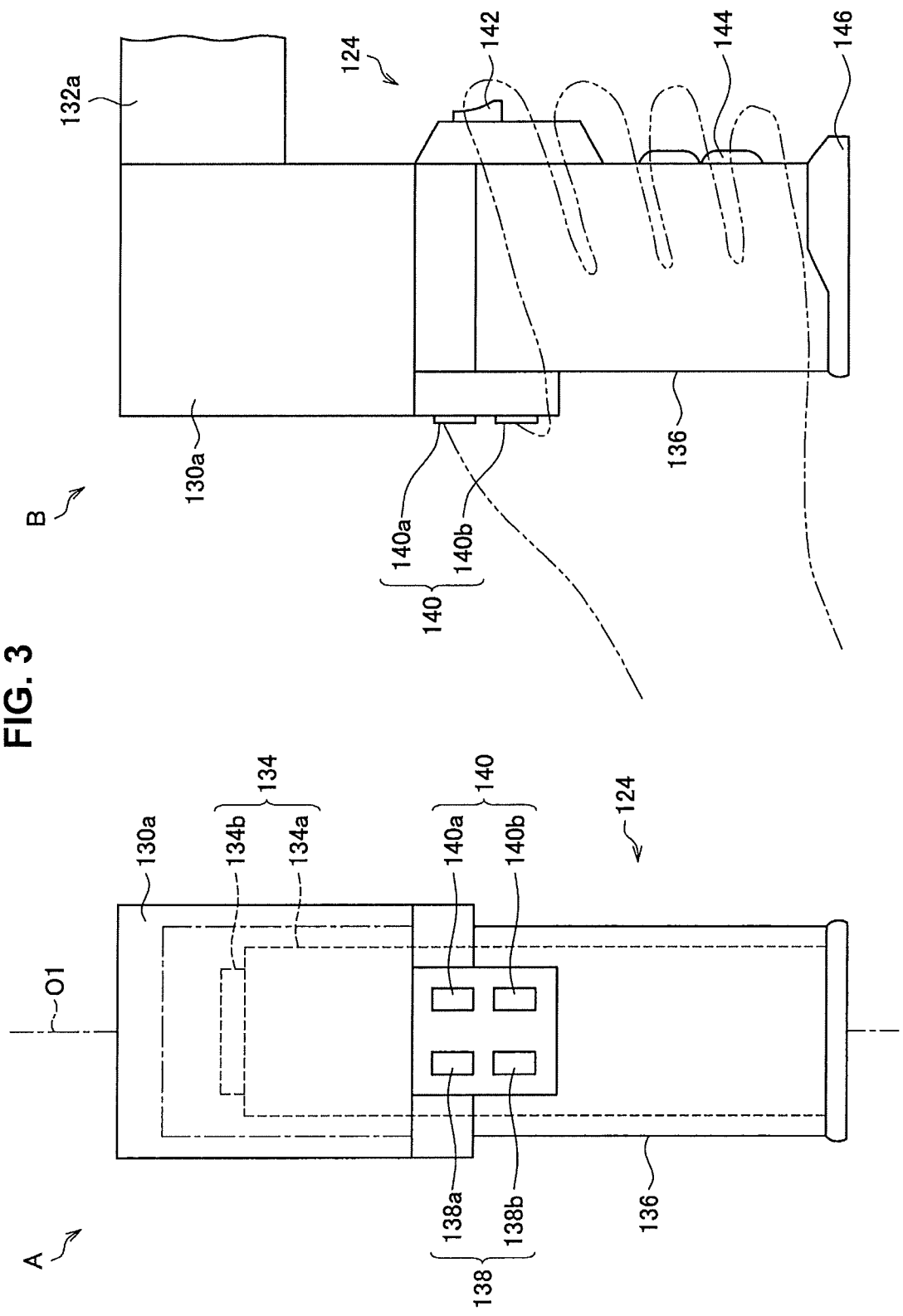
FIG. 3 shows explanatory diagrams for describing an example of a configuration of an imaging device included in the medical observation device illustrated in FIG. 2.

FIG. 3 shows explanatory diagrams for describing an example of a configuration of the imaging device 124 included in the medical observation device 100 illustrated in FIG. 2.

The imaging device 124 has, for example, an imaging member 134 and a tubular member 136 having a substantially cylindrical shape, and the imaging member 134 is provided in the tubular member 136.

Cover glass (not illustrated) for protecting the imaging member 134, for example, is provided on an opening surface of a lower end (an end on a lower side in FIG. 3) of the tubular member 136.

In addition, a light source (not illustrated) is provided, for example, inside of the tubular member 136, and during imaging, illumination light from the light source is radiated to a subject through the cover glass. Since reflected light (observation light) from the subject irradiated with the illumination light is incident on the imaging member 134 through the cover glass (not illustrated), an image signal (an image signal indicating a captured image) representing the subject is obtained by the imaging member 134.

As the imaging member 134, a configuration used in any of various known electronic imaging-type microscope unit can be applied.

To give an example, the imaging member 134 is constituted by, for example, an optical system 134a and an image sensor 134b including an image sensor that captures image of an observation target using light that has passed through the optical system 134a. The optical system 134a includes optical elements, for example, one or two or more lenses such as an objective lens, a zoom lens, and a focus lens, a mirror, and the like. As the image sensor 134b, for example, an image sensor using a plurality of image sensors such as complementary metal oxide semiconductors (CMOS), charge coupled devices (CCDs), and the like is exemplified.

The imaging member 134 may have a pair of image sensors, that is, may function as a so-called stereo camera. The imaging member 134 may have one or two or more functions included in a general electronic imaging type microscope unit, such as a zoom function (one or both of an optical zoom function and an electronic zoom function), a focus function such as auto focus (AF), and the like.

In addition, the imaging member 134 may be capable of perform imaging at so-called high resolution of, for example, 4K, 8K, or the like. When the imaging member 134 can perform imaging at high resolution, it is possible to display an image on the display device 200 having a large display screen of, for example, 50 inches or greater while predetermined resolution (e.g., full HD image quality, etc.) is secured, and thus visibility of an operator viewing the display screen is improved. In addition, when the imaging member 134 can perform imaging at high resolution, even if a captured image is enlarged using the electronic zoom function and displayed on the display screen of the display device 200, predetermined resolution can be secured. Furthermore, in a case in which predetermined resolution is secured by using the electronic zoom function, performance of the optical zoom function of the imaging device 124 can be suppressed, and thus the optical system of the imaging device 124 can be made simpler and thus the imaging device 124 can be further miniaturized.

The imaging device 124 has, for example, various operation devices for controlling operations of the imaging device 124. In FIG. 3, for example, a zoom switch 138, a focus switch 140, and an operation mode change switch 142 are provided in the imaging device 124. Note that it is a matter of course that a position at which the zoom switch 138, the focus switch 140, and the operation mode change switch 142 are provided and shapes thereof are not limited to the example illustrated in FIG. 3.

The zoom switch 138 and the focus switch 140 are an example of an operation device for adjusting imaging conditions of the imaging device 124.

The zoom switch 138 is constituted by, for example, a zoom-in switch 124a for increasing zoom magnifications (enlargement magnifications) and a zoom-out switch 124b for decreasing zoom magnifications. A zoom magnification is adjusted by performing an operation on the zoom switch 138, and thereby zoom is adjusted. Increasing a zoom magnification may be referred to as "zoom in" and decreasing a zoom magnification may be referred to as "zoom out" below.

The focus switch 140 is constituted by, for example, a distant view focus switch 140a for lengthening a focal distance to an observation target (subject) and a near-view focus switch 140b for shortening a focal distance to an observation target. By adjusting a focal distance by performing an operation on the focus switch 140, focus is adjusted. Lengthening a focal distance to an observation target may be called "focus out," and shortening a focal distance to an observation target may be called "focus in."

The operation mode change switch 142 is an example of an operation device of the imaging device 124 for changing an operation mode of the arm 122. When an operation is performed on the operation mode change switch 142, the operation mode of the arm 122 is changed. As the operation mode of the arm 122, for example, there are the fixed mode and the free mode as described above.

As an example of an operation with respect to the operation mode change switch 142, an operation of pressing the operation mode change switch 142 is exemplified. For example, while an operator presses the operation mode change switch 142, the operation mode of the arm 122 shifts to the free mode, and when the operator does not press the operation mode change switch 142, the operation mode of the arm 122 shifts to the fixed mode.

In addition, in the imaging device 124, a non-slip member 144 and a projecting member 146, for example, are provided to improve operability, convenience, and the like during operations by an operator who performs an operation with respect to the various operation devices.

The non-slip member 144 is a member provided to prevent an operating body from slipping when, for example, an operator performs an operation on the tubular member 136 using an operating body such as his or her hand. The non-slip member 144 has, for example, a material having a high friction factor, and thus has a structure which makes it difficult for an operating body to slip due to unevenness.

The projecting member 146 is a member provided to prevent an operating body from blocking a visual field of the optical system 134a when an operator operates the tubular member 136 with the operating body such as his or her hand or to prevent the cover glass (not illustrated) from becoming dirty due to contact of the cover glass with an operating body when performing an operation with the operating body.

Note that it is a matter of course that a position at which each of the non-slip member 144 and the projecting member 146 is provided and a shape thereof are not limited to the example illustrated in FIG. 3. In addition, in the imaging device 124, one or both of the non-slip member 144 and the projecting member 146 may not be provided.

An image signal (image data) generated from imaging by the imaging device 124 is subject to, for example, image processing by a processor that functions as a control unit, which will be described below. As image processing according to the present embodiment, for example, one or two or more processes among various kinds of processes including gamma correction, adjustment of white balance, image enlargement or reduction in accordance with the electronic zoom function, inter-pixel correction, and the like are exemplified. Note that, in a case in which the medical observation system according to the second example has a control device (not illustrated) that controls various operations of the medical observation device 100, image processing according to the present embodiment may be performed by the control device (not illustrated).

The medical observation device 100 transmits, for example, a display control signal and an image signal that has undergone the above-described image processing to the display device 200.

When a display control signal and an image signal are transmitted to the display device 200, the display screen of the display device 200 displays a medical captured image obtained by capturing an observation target (e.g., a captured image in which an operative site is captured) enlarged or reduced to a desired magnification using one or both of the optical zoom function and the electronic zoom function.

The medical observation device 100 that functions as the electronic imaging-type medical observation device according to the other example has, for example, the hardware configuration illustrated with reference to FIGS. 2 and 3.

Note that a hardware configuration of the medical observation device that functions as the electronic imaging-type medical observation device according to the other example is not limited to the configuration illustrated with reference to FIGS. 2 and 3.

For example, the medical observation device according to the present embodiment may have the arm 122 that is directly installed on a ceiling, a wall surface, or the like of an operating room or the like, without having the base 120. For example, in a case in which the arm 122 is installed on a ceiling, the arm 122 of the medical observation device according to the present embodiment is hung from the ceiling.

In addition, although the example in which the arm 122 realizes six degrees of freedom with respect to driving of the imaging device 124 is illustrated in FIG. 2, a configuration of the arm 122 is not limited to the configuration in which driving of the imaging device 124 has six degrees of freedom. For example, the arm 122 may appropriately move the imaging device 124 in accordance with an application, and the number and disposition of the joints and links, directions of driving axes of the joints, and the like can be appropriately set so that the arm 122 has a desired degree of freedom. To give an example, the medical observation device according to the present embodiment may have a simpler configuration of controlling an X axis and a Y axis, like an ophthalmology microscope.

In addition, although the example in which various operation devices for controlling operations of the imaging device 124 are provided in the imaging device 124 is illustrated in FIGS. 2 and 3, some or all of the operation devices illustrated in FIGS. 2 and 3 may not be provided in the imaging device 124. To give an example, various operation devices for controlling operations of the imaging device 124 may be provided in a part other than the imaging device 124 constituting the medical observation device according to the present embodiment. In addition, to give another example, various operation device for controlling operations of the imaging device 124 may be external operation devices such as a foot switch and a remote controller.

As the medical observation device 100 constituting the medical observation system 1000 according to the present embodiment, for example, a medical observation device that functions as the endoscope device illustrated in FIG. 1, a medical observation device that functions as the electronic imaging-type medical observation device according to the other example illustrated in FIG. 2, or the like is exemplified.

[2] Control Method According to the Present Embodiment
[2-1] Overview of Control Method According to the Present Embodiment In an existing medical observation system in which a medical observation device such as an existing endoscope is used as described above, a medical captured image displayed on a display screen may not be an image in which an operative site that an operator desires to observe can be easily viewed. In addition, in order to gain a medical captured image in which an operative site that an operator desires to observe can be easily viewed, for example, an operation of making an image with a favorable S/N is necessary by adjusting intensity of illumination. Thus, with regard to an existing medical observation system, there is concern of convenience of medical staff such an operator, an assistant of the operator, or a scopist being impaired.

Therefore, in the medical observation system 1000, the medical observation device 100 controls at least an exposure function of an imaging device (the process relating to the control method according to the present embodiment) using, for example, a line of sight detected having a specific person such as an operator as a recognition target.

Detection of a line of a sight of a recognition target is performed by, for example, a line-of-sight detection sensor of the medical observation system 1000. For example, in a case in which the line-of-sight detection sensor is a sensor unit having a stereo camera, the line-of-sight detection sensor is provided to perform imaging in the front direction of the display screen (e.g., a perpendicular direction to the plane corresponding to the display screen) on which a medical captured image is displayed.

In the medical observation system 1000, a recognition target is specified by performing a face detection process of detecting a face set in an image captured by the line-of-sight detection sensor. In addition, in the medical observation system 1000, by performing a line-of-sight detection process of detecting a line-of-sight on the specified recognition target on the basis of the image captured by the line-of-sight detection sensor, the detection result of the line of sight of the recognition target is obtained.

As a detection result of a line of sight of a recognition target, for example, a line-of-sight vector indicating a line of sight of a recognition target is exemplified. In addition, a detection result of a line of sight of a recognition target may be, for example, a position of the line of sight of the recognition target on a display screen on which a medical captured image is displayed. A position of a line of sight of a recognition target on a display screen is specified by, for example, obtaining an intersection of a line-of-sight vector with a plane corresponding to the display screen and expressed by two-dimensional coordinates having an arbitrary position of the display screen as the origin.

One or both of the face detection process and the line-of-sight detection process in the medical observation system 1000 may be performed by the line-of-sight detection sensor, or by the medical observation device 100, the control device (not illustrated), or the display device 200. Note that it is a matter of course that a method of detecting a line of sight of a recognition target according to the present embodiment is not limited to the above-described example.

In addition, detection of a line of sight of a recognition target in the medical observation system 1000 may be stopped by an operation of a user of the medical observation system 1000, and the stop may be cancelled by an operation of a user of the medical observation system 1000. As an operation relating to detection of a line of sight of a recognition target, for example, an operation with respect to an operation device such as a foot switch, an operation using a motion such as a gesture, an operation using a voice, or the like is exemplified.

By enabling detection of a line of sight of a recognition target to be stopped, a state in which the line of sight of the recognition target is fixed can be realized without imposing a strain on the recognition target.

Since the medical observation device 100 controls the exposure function of the imaging device on the basis of a detection result of a line of sight of a recognition target, a medical captured image displayed on the display screen can be automatically made into an "image in which an operative site that a specific person who is a recognition target desires to observe can be easily viewed."

Therefore, since the medical observation device 100 controls the exposure function of the imaging device on the basis of the detection result of the line of sight of the specific person, the medical observation system 1000 that can achieve enhancement in convenience is realized.

The medical observation system 1000 to which the control method according to the present embodiment is applied will be described along with description of functions of respective devices constituting the medical observation system 1000. In addition, a case in which the medical observation system 1000 according to the present embodiment is the medical observation system 1000 according to the first example illustrated in FIG. 1 will be mainly described below.

[2-2] Medical Observation Device 100

Figure 4:
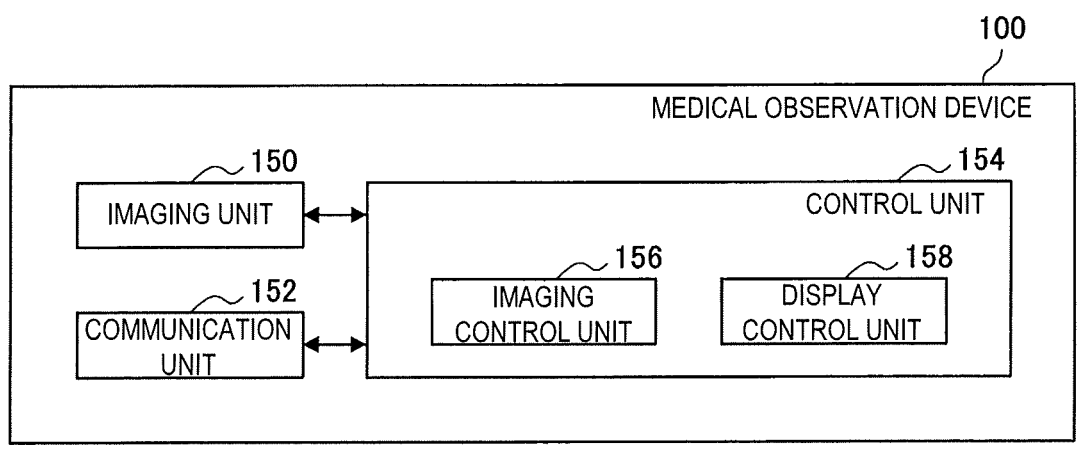
FIG. 4 is a functional block diagram illustrating an example of a configuration of a medical observation device according to an embodiment of the present disclosure.

FIG. 4 is a functional block diagram illustrating an example of a configuration of the medical observation device 100 according to the present embodiment. The medical observation device 100 includes, for example, an imaging unit 150, a communication unit 152, and a control unit 154.

[2-2-1] Imaging Unit 150

The imaging unit 150 captures observation targets. In a case in which the medical observation device 100 has the configuration illustrated in FIG. 1, the imaging unit 150 is constituted by the insertion member 102, the light source unit 104, and the camera head 108 (members playing the role of an imaging device in the medical observation device 100 illustrated in FIG. 1). In addition, in a case in which the medical observation device 100 has the configuration illustrated in FIG. 2, the imaging unit 150 is constituted by the imaging device 124. Imaging performed by the imaging unit 150 is controlled by, for example, the control unit 154.

[2-2-2] Communication Unit 152

The communication unit 152 is a communication section of the medical observation device 100, and plays the role of performing wireless or wired communication with an external device such as the display device 200. The communication unit 152 is constituted by, for example, the above-described communication device (not illustrated). Communication performed by the communication unit 152 is controlled by, for example, the control unit 154.

[2-2-3] Control Unit 154

The control unit 154 plays a role of controlling the entire medical observation device 100. In addition, the control unit 154 plays the leading role of performing the process relating to the control method according to the present embodiment.

In the case in which the medical observation device 100 has the configuration illustrated in FIG. 1, the control unit 154 is constituted by, for example, the control unit 112. In addition, in the case in which the medical observation device 100 has the configuration illustrated in FIG. 2, the control unit 154 is constituted by, for example, the above-described processor (not illustrated). Note that the process relating to the control method by the control unit 154 may be distributed to be performed by a plurality of processing circuits (e.g., a plurality of processors and the like).

More specifically, the control unit 154 has, for example, an imaging control unit 156 and a display control unit 158.

[2-2-3-1] Imaging Control Unit 156

The imaging control unit 156 controls the imaging device constituting the imaging unit 150. As control over the imaging device 124, for example, control of one or two or more imaging functions through which imaging of the imaging device can be controlled, such as control of the zoom function (one or both of the optical zoom function and the electronic zoom function) including at least the exposure function, control of the focus function such as AF, control of a shutter speed function to control a refresh rate of an image sensor, and the like are exemplified.

The imaging control unit 156 controls, for example, a light source such as the light source unit 104 and the exposure function by controlling illumination light radiated to an observation target such as a lesion. In addition, the imaging control unit 156 may control the exposure function by, for example, controlling a gain with respect to an image signal indicating a medical captured image. As an example of a process relating to control of a gain with respect to an image signal, for example, signal processing of averaging luminance of a medical captured image is exemplified.

More specifically, the imaging control unit 156 controls the exposure function of the imaging device on the basis of a detection result of a line of sight of a recognition target so that luminance of a predetermined region of a medical captured image is changed. The imaging control unit 156 controls the exposure function of the imaging device on the basis of, for example, a position of a line of sight of recognition target (an example of a detection result of a line of sight of a recognition target or an example of information specified from a detection result of a line of sight of a recognition target) on the display screen on which a medical captured image is displayed so that luminance of a predetermined region of the medical captured image is changed.

The imaging control unit 156 changes luminance of a predetermined region by controlling the exposure function of the imaging device so that, for example, luminance of the predetermined region of the medical captured image increases or luminance of the predetermined region is decreased. The predetermined region becomes brighter by increasing the luminance of the predetermined region of the medical captured image, or the predetermined region becomes darker by decreasing the luminance of the predetermined region. The imaging control unit 156 controls the exposure function of the imaging device so that the luminance of the predetermined region in the medical captured image increases in a case in which a line of sight of a recognition target moves from a bright operative site to a dark operative site, for example, a case in which the line of sight of the recognition target moves from a front operative site to a deep operative site. In addition, the imaging control unit 156 controls the exposure function of the imaging device so that luminance of a predetermined region of a medical captured image is decreased in a case in which a line of sight of a recognition target moves from a dark operative site to a bright operative site, for example, a case in which the line of sight of the recognition target moves from a deep operative site to a front operative site. Since the imaging control unit 156 controls the exposure function of the imaging device as described above, for example, it is possible to make it easier to view a predetermined region of a medical captured image.

The imaging control unit 156 controls the exposure function of the imaging device by controlling intensity of illumination light so that, for example, the average of brightness of a predetermined region of a medical captured image is uniform and averaging luminance through signal processing.

Readiness for control of the exposure function based on a detection result of a line of sight of a recognition target is determined using, for example, calibration performed on the recognition target or a value set in a statistical method, or the like.

As a predetermined region according to the present embodiment, for example, a "region in which a position in a medical captured image corresponding to a position of a light of sight on a display screen is included" is exemplified. A position of a line of sight on a display screen is expressed by, for example, two-dimensional coordinates having an arbitrary position on the display screen as the origin as described above. In addition, a position in a medical captured image corresponding to a position of a line of sight on a display screen is expressed by, for example, two-dimensional coordinates having an arbitrary position on a medical captured image as the origin. Hereinbelow, a "position in a medical captured image corresponding to a position of a line of sight on a display screen" may be referred to simply as a "position in a medical captured image."

The imaging control unit 156 transforms a position of a line of sight on the display screen into a position in a medical captured image and sets a predetermined region to include the position in the medical captured obtained from the transform. The imaging control unit 156 transforms the position of the line of sight on the display screen into the position in the medical captured image, for example, by using a transformation matrix stored in the recording medium (not illustrated). Note that the imaging control unit 156 may transform the position of the line of sight on the display screen into the position in the medical captured image by performing an arithmetic operation of an arbitrary algorithm in which a coordinate transformation can be performed.

In addition, as a predetermined region, for example, regions introduced in the following examples are exemplified.

Region of which shape and size are set in advance
Region of which shape and size are set for each recognition target
Region of which one or both of shape and size are changed in accordance with a movement of a line of sight The imaging control unit 156 specifies a shape and a size of a predetermined region set in advance with reference to, for example, "region data of a region of which a shape and a size are set in advance" stored in the recording medium (not illustrated). In addition, the imaging control unit 156 specifies a shape and a size of a predetermined region corresponding to a recognition target with reference to, for example, a "table (or database) in which data indicating the recognition target (e.g., a user ID or the like) is associated with region data" stored in the recording medium (not illustrated). In addition, the imaging control unit 156 specifies a shape and a size of a predetermined region corresponding to a movement of a line of sight with reference to, for example, a "table (or database) in which a movement amount of the line of sight is associated with region data" stored in the recording medium (not illustrated). A movement amount of a line of sight is determined on the basis of, for example, a Euclidean distance between a "position of the line of sight on the display screen at a first time point" and a "position of the line of sight on the display screen at a second time point (a time point later than the first time point)."

Note that a predetermined region according to the present embodiment is not limited to the above-described examples. The imaging control unit 156 may set a predetermined region by, for example, performing an arithmetic operation of an arbitrary algorithm in which a region can be set every time.

As control of the exposure function by the imaging control unit 156, for example, one or both of control of illumination light radiated from a light source such as the light source unit 104 and control of a gain with respect to an image signal indicating a medical captured image are exemplified. In addition, as control of illumination light, for example, one or two or more of control of illuminance of illumination light, control of a type of illumination light, and control of a radiation time of illumination light (an example of control of an exposure time) are exemplified.

To give an example, as control of the exposure function by the imaging control unit 156, for example, one or both of a first example introduced in (A) and a second example introduced in (B) below are exemplified. Note that an example of control of the exposure function according to the present embodiment is not limited to the following examples, and arbitrary control by which exposure can be changed so that luminance of a predetermined region in a medical captured image is changed is possible.

(A) First example of Control of Exposure Function

The imaging control unit 156 controls the exposure function so that luminance of a region other than a predetermined region in a medical captured image is decreased. The imaging control unit 156 decreases luminance of the region other than the predetermined region through control of a gain with respect to an image signal indicating the medical captured image.

To give an example, the imaging control unit 156 decreases luminance of the region other than the predetermined region so that the luminance of the region other than the predetermined region has a value equal to or smaller than a set threshold value (or the luminance of the region other than the predetermined region has a value smaller than the threshold value). In addition, to give another example, the imaging control unit 156 decreases luminance of the region other than the predetermined region so that the luminance of the region other than the predetermined region has a value smaller than an average value of luminance of the predetermined region.

The imaging control unit 156 performs control of the exposure function according to the first example on the basis of, for example, a detection result of a line of sight of a recognition target. To give an example, the imaging control unit 156 performs the control of the exposure function according to the first example in a case in which a "state in which a change of a position of a line of sight on the display screen in a set first period is smaller than a set threshold value (or a state in which the change of the position of the line of sight on the display screen in the first period is equal to or smaller than the threshold value)" continues for a set second period or longer (or continues longer than the second period). For example, by performing the control of the exposure function according to the first example on the basis of the detection result of the line of sight of the recognition target as described above, a visual effect as if an operative site is irradiated with spot illumination light when an operator (an example of the recognition target) gazes the operative site is realized.

Note that a trigger for the control of the exposure function according to the first example is not limited to a detection result of a line of sight of a recognition target. For example, the imaging control unit 156 may perform the control of the exposure function according to the first example on the basis of a predetermined operation such as an operation performed on an operation device such as a foot switch, a gesture operation, or a voice operation. In addition, the imaging control unit 156 may switch from the control of the exposure function according to the first example to other control of the exposure function such as control of the exposure function according to the second example, which will be described below, on the basis of a predetermined operation such as an operation with respect to the operation device.

In addition, the imaging control unit 156 may control the zoom function of the imaging device so that electronic zoom is performed with respect to a predetermined region in conjunction with the control of the exposure function according to the first example. The control of the zoom function in conjunction with the control of the exposure function according to the first example may be automatically performed, or performed on the basis of a predetermined operation such as an operation performed on an operation device such as a foot switch, a gesture operation, or a voice operation. In addition, the control of the zoom function in conjunction with the control of the exposure function according to the first example, for example, can be cancelled on the basis of a predetermined operation such as an operation performed on an operation device.

To exemplify a case in which an operator is a line-of-sight recognition target, by performing the control of the zoom function in conjunction with the control of the exposure function according to the first example, a medical staff member such as the operator or an assistant of the operator can conduct medical practice viewing an "enlarged medical captured image that seems to be captured as if an operative site that the operator desires to observe was irradiated with spot illumination." Thus, by performing the control of the zoom function in conjunction with the control of the exposure function according to the first example, the medical captured image in which the operative site that the operator desires to observe can be viewed more easily can be displayed on the display screen, and thus convenience of medical staff can be further improved.

(B) Second Example of Control of Exposure Function

The imaging control unit 156 controls the exposure function such that diffused illumination light is radiated to a position of an observation target corresponding to a position in a medical captured image.

The imaging control unit 156 controls the imaging device so that, for example, the center of an optical axis of diffused illumination light comes at an estimated position of an observation target. In the case in which the medical observation device 100 has the configuration illustrated in FIG. 1, the imaging control unit 156 causes diffused illumination light to be radiated to the position of the observation target by controlling, for example, a mechanism (not illustrated) that adjusts an incidence angle of illumination light to a diffuser constituting the light source unit 104 and the light guide 106. In a case in which the medical observation device 100 has the configuration illustrated in FIG. 1 and the insertion member 102 has a material having flexibility (i.e., a flexible mirror), diffused illumination light may be radiated to the position of the observation target by moving the center of the optical axis of the diffused illumination light. In addition, in the case in which the medical observation device 100 has the configuration illustrated in FIG. 2, the imaging control unit 156 causes diffused illumination light to be radiated to the position of the observation target by, for example, controlling the diffuser constituting the light source (not illustrated) and the arm 122. Note that it is a matter of course that a method of controlling the exposure function such that diffused illumination light is radiated to a position of an observation target is not limited to the above-described example.

The imaging control unit 156 performs the control of the exposure function according to the second example on the basis of, for example, a predetermined operation such as an operation performed on an operation device such as a foot switch, a gesture operation, or a voice operation. In addition, the imaging control unit 156 may automatically perform the control of the exposure function according to the second example and switch to the above-described control of the exposure function according to the first example on the basis of a detection result of a line of sight of a recognition target, or the like.

Here, switching between the above-described control of the exposure function according to the first example and control of the exposure function according to the second example can be realized on the basis of the fact that, for example, "the light source unit 104 has a diffuser insertion/removal mechanism."

FIG. 5 shows explanatory diagrams for describing the control method according to the present embodiment. A of FIG. 5 schematically illustrates a diffuser insertion/removal mechanism included in the light source unit 104 illustrated in FIG. 1, and B of FIG. 5 shows differences in radiation angles depending on the presence or absence of a diffuser.

As shown in B of FIG. 5, a radiation angle changes from X[°] to Y[°] (Y>X) and an illuminated region is widened since a diffuser has been inserted. In addition, illumination light with higher illuminance can be radiated to the illuminated region as shown in B of FIG. 5 without changing illuminance of the illumination light radiated from the light source unit 104 since the diffuser has been inserted.

[2-2-3-2] Display Control Unit 158

The display control unit 158 controls display of the display device 200 by, for example, transferring a display control signal and an image signal to the communication device (not illustrated) constituting the communication unit 152 and causing the display control signal and the image signal to be transmitted to the display device 200. Note that control over communication of the communication unit 152 may be performed by a communication control unit (not illustrated) constituting the control unit 154.

In addition, the display control unit 158 may perform, for example, one or two or more kinds of display control among display control introduced in a first example of (a) below to a fourth example of (d) below.

(a) First Example of Display Control

The display control unit 158 causes a position in a medical captured image corresponding to a position of a line of sight on the display screen to be displayed on the display screen on the basis of a detection result of the line of sight of a recognition target.

The display control unit 158 causes the position in the medical captured image to be displayed on the display screen by, for example, causing a predetermined region in which the position in the medical captured image is included to be displayed on the display screen.

Figure 6:
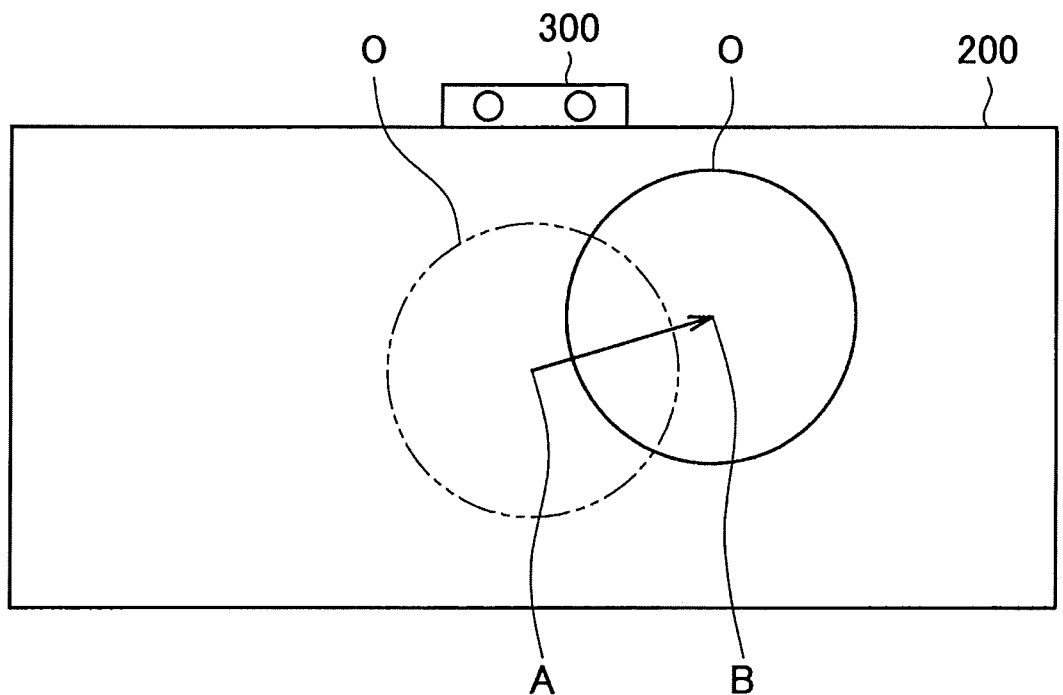
FIG. 6 is an explanatory diagram for describing the control method according to an embodiment of the present disclosure.

FIG. 6 is an explanatory diagram for describing the control method according to the present embodiment, showing an example in which a predetermined region in which a position in a medical captured image is included is displayed on the display screen of the display device 200. In FIG. 6, a line-of-sight detection sensor 300 serving as a sensor unit having a stereo camera is also shown. In addition, reference sign O shown in FIG. 6 represents the predetermined region in which the position in the medical captured image is included, and an example in which the predetermined region is a circular region having the position in the medical captured image as the center. Note that it is a matter of course that a shape and a size of the predetermined region is not limited to the example shown in FIG. 6.

In a case in which the position of the line of sight on the display screen is changed from a position A to a position B shown in FIG. 6, the display control unit 158 moves display of the predetermined region in which the position in the medical captured image is included to match the change of the position of the line of sight on the display screen.

Here, in a case in which an observation target faces the imaging device and illumination light and is a uniform plane, intensity of the illumination light does not change and a change in luminance caused by signal processing does not occur even the line of sight of the recognition target moves.

In addition, since the region other than the predetermined region in the medical captured image is not subject to the control of the exposure function, halation is likely to occur in a case in which illumination is excessively strong, and an image thereof becomes dark in a case in which illumination is weak. However, since the region other than the predetermined region does not includes a position of a line of sight of a recognition target, there is no concern of control of the region affecting medical practice conducted by an operator (an example of a recognition target).

Note that an example of causing a position in a medical captured image to be displayed on a display screen is not limited to displaying a predetermined region in which a position in a medical captured image is included on the display screen as illustrated in FIG. 6. For example, the display control unit 158 may cause a position in a medical captured image to be displayed on the display screen by, for example, causing an image signal indicating a "medical captured image on which an object indicating a position in the medical captured image (e.g., an object indicating a position in the medical captured image like an arrow, etc.) is superimposed" to be transmitted to the display device 200.

To give an example of a case in which an operator is a recognition target of a line of sight, by performing the display control according to the first example described above, other medical staff members, for example, an assistant of the operator, a scopist, a nurse, and the like can visually recognize an operative site that the operator is viewing. Thus, by performing the display control according to the first example described above, the effect of more smooth communication between the medical staff members using the medical observation system 1000 is expected.

In addition, to give another example of the case in which an operator is a recognition target of a line of sight, by performing the display control according to the first example described above, a preceptor who instructs the operator, for example, can visually recognize the operative site that the operator is viewing. Thus, by performing the display control according to the first example described above, the effect that the operator can be effectively educated by the preceptor is expected.

(b) Second Example of Display Control

The display control unit 158 causes a user interface image for controlling the imaging functions of the imaging device to be displayed on the display screen.

As a user interface image for controlling the imaging functions of the imaging device, an image for operating one or two or more imaging functions of the imaging device such as the zoom function (one or both of the optical zoom function and the electronic zoom function), the focus function, the exposure function, and a shutter speed function is exemplified. In the user interface image for controlling the imaging functions of the imaging device, each of the imaging functions may be displayed using an icon or a letter.

Figure 7:
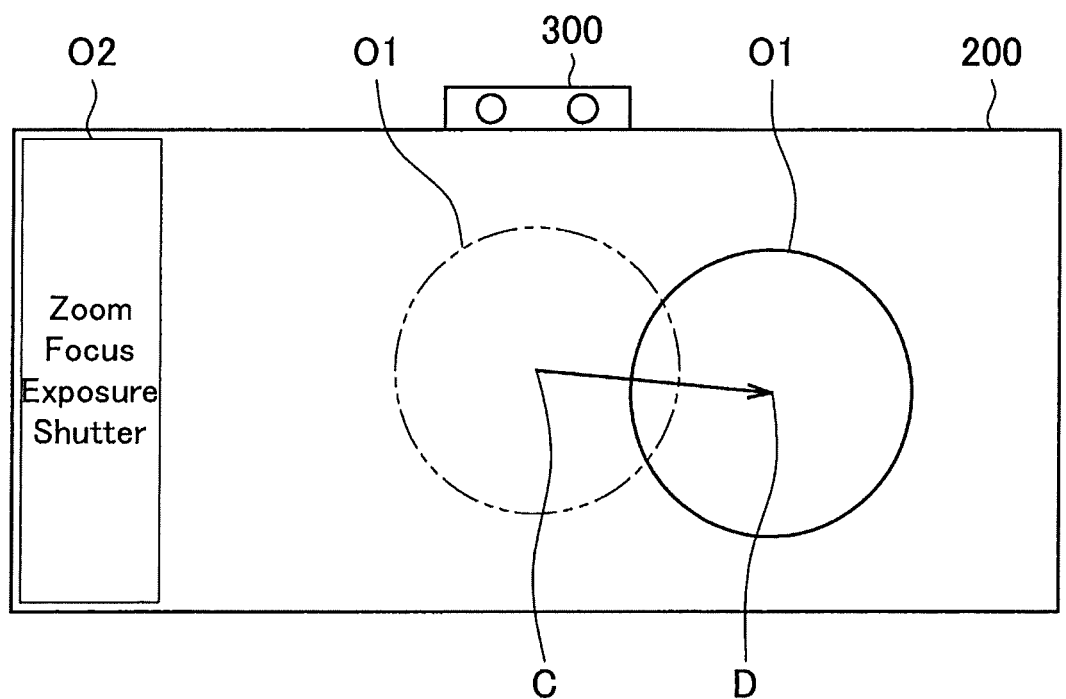
FIG. 7 is an explanatory diagram for describing the control method according to an embodiment of the present disclosure.

FIG. 7 is an explanatory diagram for describing the control method according to the present embodiment, showing an example in which a user interface image for controlling the imaging functions of the imaging device is displayed on the display screen of the display device 200 in addition to similar display to FIG. 6. In FIG. 7, the line-of-sight detection sensor 300 serving as a sensor unit having a stereo camera is also shown as in FIG. 6. Reference sign O1 shown in FIG. 7 represents a predetermined region in which a position in a medical captured image is included, similarly to reference sign O shown in FIG. 6. In addition, reference sign O2 shown in FIG. 7 represents an example of the user interface image for controlling the imaging functions of the imaging device. Note that it is a matter of course that a user interface image for controlling the imaging functions of the imaging device is not limited to the example illustrated in FIG. 7.

In a case in which a position of a line of sight on the display screen is changed from a position C to a position D shown in FIG. 7, the display control unit 158 moves display of the predetermined region in which the position in the medical captured image is included to correspond to the change of the position of the line of sight on the display screen.

In addition, in a case in which an operation is performed on the user interface image for controlling the imaging functions of the imaging device, for example, an operation of an operation device, a gesture operation, a voice operation, or the like, the display control unit 158 changes display of the user interface image to correspond to the operation. In addition, the imaging control unit 156 controls an imaging function corresponding to an operation performed on the user interface image for controlling the imaging functions of the imaging device.

Note that display control according to the second example is not limited to the above-described examples.

For example, the display control unit 158 may cause a position of a line of sight of a recognition target on the user interface image to be displayed on the display screen on the basis of a detection result of the line of sight of the recognition target.

To give an example of the case in which an operator is a recognition target of a line of sight, by displaying a position of a line of sight of the operator on the user interface image on the display screen, other medical staff members such as an assistant of the operator can notice intention of the operator and perform an operation on the user interface image.

In addition, the display control unit 158 may cause a user interface image for controlling the function other than the imaging functions of the imaging device of the medical observation device 100 and a user interface image for controlling a function of an apparatus other than the medical observation device 100 to be displayed on the display screen.

(c) Third Example of Display Control

The display control unit 158 causes a state of the imaging functions of the imaging device to be displayed on the display screen.

As display of a state of the imaging functions of the imaging device, for example, display of a value indicating a zoom magnification, display of an F number (aperture value), display of an exposure value (EV), display of a shutter speed value, or the like is exemplified.

Note that display control according to the third example is not limited to the above-described example.

For example, the display control unit 158 may cause a position of a line of sight of a recognition target on the display screen on which a state of the imaging functions of the display device has been displayed to be displayed on the display screen on the basis of a detection result of a line of sight of a recognition target.

(d) Fourth Example of Display Control

The display control unit 158 may cause a "vital sign of a patient," an "image output from a navigation device," an "image showing a setting of a treatment device among various treatment devices such as an electric scalpel, bipolar forceps, an ultrasonic aspirator," or the like to be displayed on the display screen. The display control unit 158 causes a value or an image acquired from an external device such as a device that measures vital conditions to be displayed on the display screen.

Note that display control according to the fourth example is not limited to the above-described example.

For example, the display control unit 158 may cause a position of a line of sight of a recognition target on the display screen on which a "vital sign of a patient" or the like is displayed to be displayed on the display screen on the basis of a detection result of the line of sight of the recognition target.

To give an example of the case in which an operator is a recognition target of a line of sight, a mechanism that helps another medical staff member transfer new information regarding information at the tip of the line of sight of the operator to the operator when a line of sight of the operator is at a position on the display screen on which a vital condition of patient or the like is displayed can be realized.

The control unit 154 has a leading role of performing the process relating to the control method according to the present embodiment, for example, having the imaging control unit 156 and the display control unit 158.

Note that a configuration of the control unit 154 is not limited to the example illustrated in FIG. 4.

In the case in which the medical observation device 100 has the configuration illustrated in FIG. 1, for example, the control unit 154 may have a processing unit (not illustrated) that causes a robot that operates the medical observation device 100 (a rigid endoscope or a flexible endoscope) to move on the basis of a detection result of a line of sight of a recognition target. When the processing unit (not illustrated) transmits a control signal corresponding to the detection result of the line of sight of the recognition target to the robot, an operation of a rigid endoscope or an operation of a flexible endoscope by the robot is realized.

In addition, in the case in which the medical observation device 100 has the configuration illustrated in FIG. 2, for example, the control unit 154 may have an arm control unit (not illustrated) that controls driving of the arm 122. As an example of control of driving of the arm 122, for example, "application of a control signal for controlling driving to the actuator (not illustrated) corresponding to each of the joints 130*a*, 130*b*, 130*c*, 130*d*, 130*e*, and 130*f*" or the like is exemplified.

In addition, the control unit 154 can have an arbitrary configuration corresponding to a method of dividing the functions of the medical observation device 100, such as a configuration corresponding to a method of dividing the process relating to the control method according to the present embodiment, or the like.

By having the functions illustrated in, for example, FIG. 4, the medical observation device 100 performs the process relating to the control method according to the present embodiment.

Note that a configuration of the medical observation device according to the present embodiment is not limited to the configuration illustrated in FIG. 4.

For example, the medical observation device according to the present embodiment can have one or both of the imaging control unit 156 and the display control unit 158 illustrated in FIG. 4 separately from the control unit 154 (e.g., the imaging control unit 156 and the display control unit 158 can be realized as a separate processing circuit).

In addition, a configuration of the medical observation device according to the present embodiment for realizing the process relating to the control method according to the present embodiment is not limited to the configuration illustrated in FIG. 4, for example, and the medical observation device according to the present embodiment can have a configuration corresponding to a method of dividing the process relating to the control method according to the present embodiment.

In addition, in a case in which communication is performed with an external device via an external communication device having a similar function and configuration to the communication unit 152, for example, the medical observation device according to the present embodiment may not include the communication unit 152.

In addition, in a case in which the medical observation system according to the present embodiment has a control device (not illustrated) and the medical observation device according to the present embodiment is controlled by the control device (not illustrated), the medical observation device according to the present embodiment may not include the control unit 154.

Here, when the control device (not illustrated) includes a control unit having a similar function and configuration to the control unit 154, for example, the control device performs the process relating to the control method according to the present embodiment, which will be described below, and controls operations of each constituent element such as the imaging unit 150 or an arm unit (not illustrated) included in the medical observation device according to the present embodiment. When the control device (not illustrated) communicates with the medical observation device according to the present embodiment via the included communication device or a connected external communication device, the control device controls operations of each constituent element included in the medical observation device according to the present embodiment.

Furthermore, in a case in which the medical observation system according to the present embodiment has a control device (not illustrated) and the medical observation device according to the present embodiment is controlled by the control device (not illustrated), the medical observation device according to the present embodiment can also have a configuration without some of the functions of the control unit 154.

[2-2-4] Example of Hardware Configuration of Medical Observation Device 100

Figure 8:
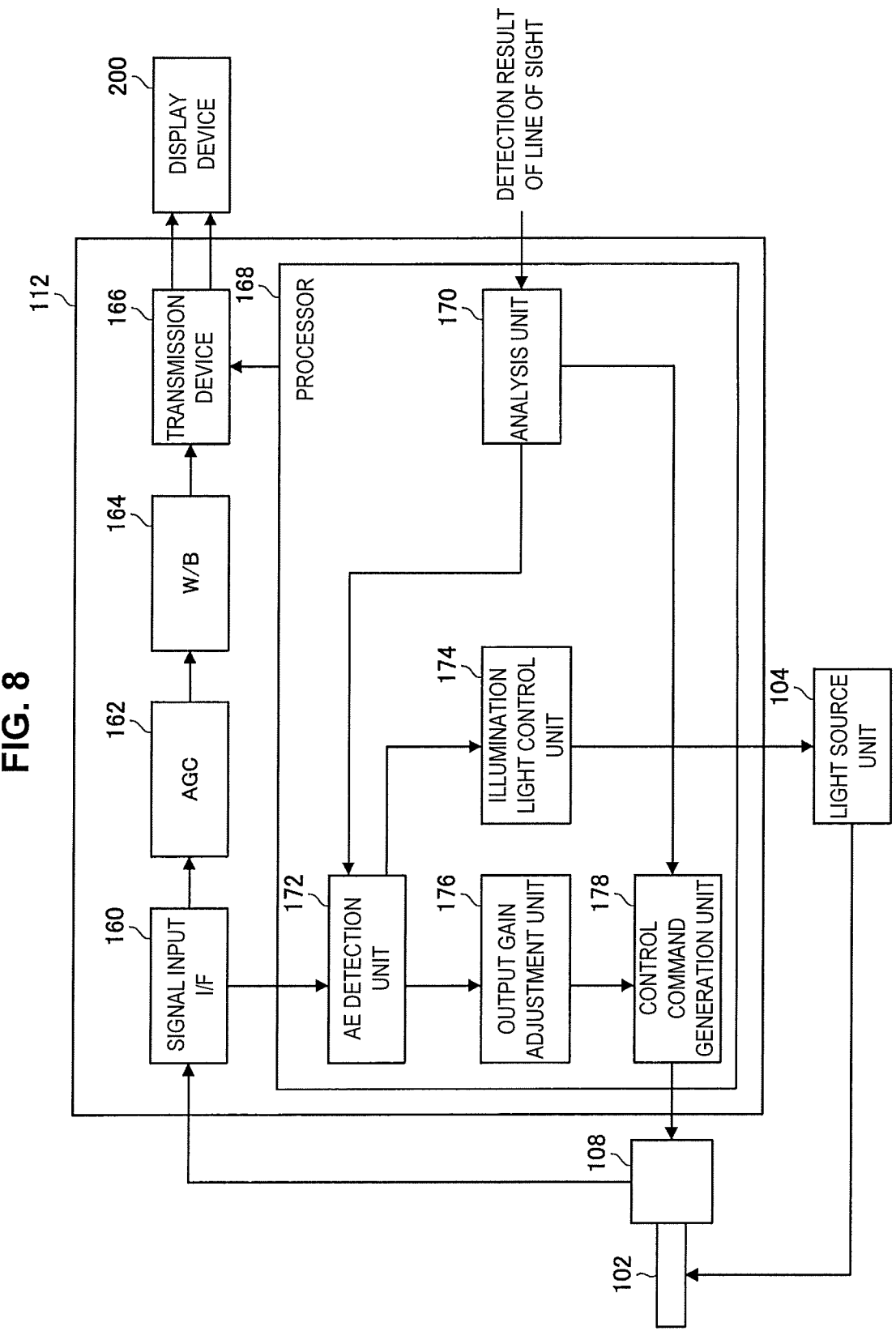
FIG. 8 is an explanatory diagram for describing an example of a hardware configuration of the medical observation device that can perform a process according to the control method according to an embodiment of the present disclosure.

Next, an example of a hardware configuration of the medical observation device 100 that can perform the process relating to the control method according to the present embodiment will be described. FIG. 8 is an explanatory diagram for describing an example of a hardware configuration of the medical observation device 100 that can perform the process according to the control method according to the present embodiment, showing an example of a configuration of the control unit 112 illustrated in FIG. 1.

The control unit 112 has, for example, a signal input interface 160, an AGC circuit 162, a white balance circuit 164, a transmission device 166, and a processor 168. In FIG. 8, the signal input interface 160 is denoted by "signal input I/F," the AGC circuit 162 is denoted by "AGC (Automatic Gain Control)," and the white balance circuit 164 is denoted by "W/B."

The signal input interface 160 is a communication interface to which signals are input, and image signals obtained from imaging by the camera head 108 are transferred to the signal input interface 160. As an image signal transferred from the camera head 108, for example, a signal indicating a raw image is exemplified.

An image signal input to the signal input interface 160 is subject to gain control in the AGC circuit 162 and to adjustment of white balance in the white balance circuit 164.

The transmission device 166 transmits, for example, the image signal that has undergone various kinds of signal processing in the AGC circuit 162 and the white balance circuit 164 and a display control signal to the display device 200. The transmission device 166, for example, performs signal processing on the image signal in accordance with an output format and transmits the signal-processed image signal.

In addition, the transmission device 166 may transmit, for example, data indicating a state of an imaging function of the imaging device such as a value indicating a zoom magnification, an F number, an EV, or a shutter speed value to the display device 200. Transmission by the transmission device 166 is controlled by the processor 168.

The processor 168 is constituted by an arithmetic circuit such as an MPU and various processing circuits, and plays a leading role of performing the process relating to the control method according to the present embodiment.

The processor 168 has, for example, an analysis unit 170, an AE detection unit 172, an illumination control light unit 174, an output gain adjustment unit 176, and a control command generation unit 178.

The analysis unit 170 analyzes data indicating a detection result of a line of sight acquired from an external device such as the line-of-sight detection sensor 300 or the display device 200, and transfers a control signal corresponding to the analysis result to each of the AE detection unit 172 and the control command generation unit 178. In a case in which it is necessary to change an exposure detection range of as a result of the analysis, for example, the analysis unit 170 transfers a control signal for changing the exposure detection range to the AE detection unit 172. In addition, in a case in which it is necessary to control various imaging functions of the camera head 108 as a result of the analysis, for example, the analysis unit 170 transfers a control signal for controlling the imaging functions to the control command generation unit 178.

The AE detection unit 172 acquires an exposure detection value on the basis of an image signal input to the signal input interface 160. The exposure detection value is calculated on the basis of, for example, a luminance value acquired from the image signal. The exposure detection range of the AE detection unit 172 can be changed in accordance with a control signal transferred from the analysis unit 170. The AE detection unit 172 transfers the acquired exposure detection value to each of the illumination control light unit 174 and the output gain adjustment unit 176.

The illumination control light unit 174 controls the light source unit 104 on the basis of the exposure detection value transferred from the AE detection unit 172 to adjust radiated illumination light from the light source unit 104.

The output gain adjustment unit 176 changes an output gain of the image sensor on the basis of the exposure detection value transferred from the AE detection unit 172.

The control command generation unit 178 generates a command for controlling the camera head 108 on the basis of each of the control signal transferred from the analysis unit 170 and the result of the changed output gain transferred from the output gain adjustment unit 176 and outputs the generated command to the camera head 108.

With the configuration of the control unit 112 illustrated in FIG. 8, for example, the process relating to the control method according to the present embodiment can be realized. Note that it is a matter of course that a configuration that makes it possible to perform the process relating to the control method according to the present embodiment is not limited to the configuration illustrated in FIG. 8.

[2-3] Display Device 200

The display device 200 displays a medical captured image indicated by an image signal transmitted from the medical observation device 100 on the display screen.

In addition, the display device 200 may have, for example, one or both of the function of detecting a line of sight on the basis of a detection result of the line-of-sight detection sensor 300 and the function of causing the line of sight to be displayed on the display screen on the basis of the detection result of the line of sight.

An example of a hardware configuration of the display device 200 having both the function of detecting a line of sight and the function of causing the line of sight to be displayed on the display screen on the basis of the detection result of the line of sight will be shown below.

Figure 9:
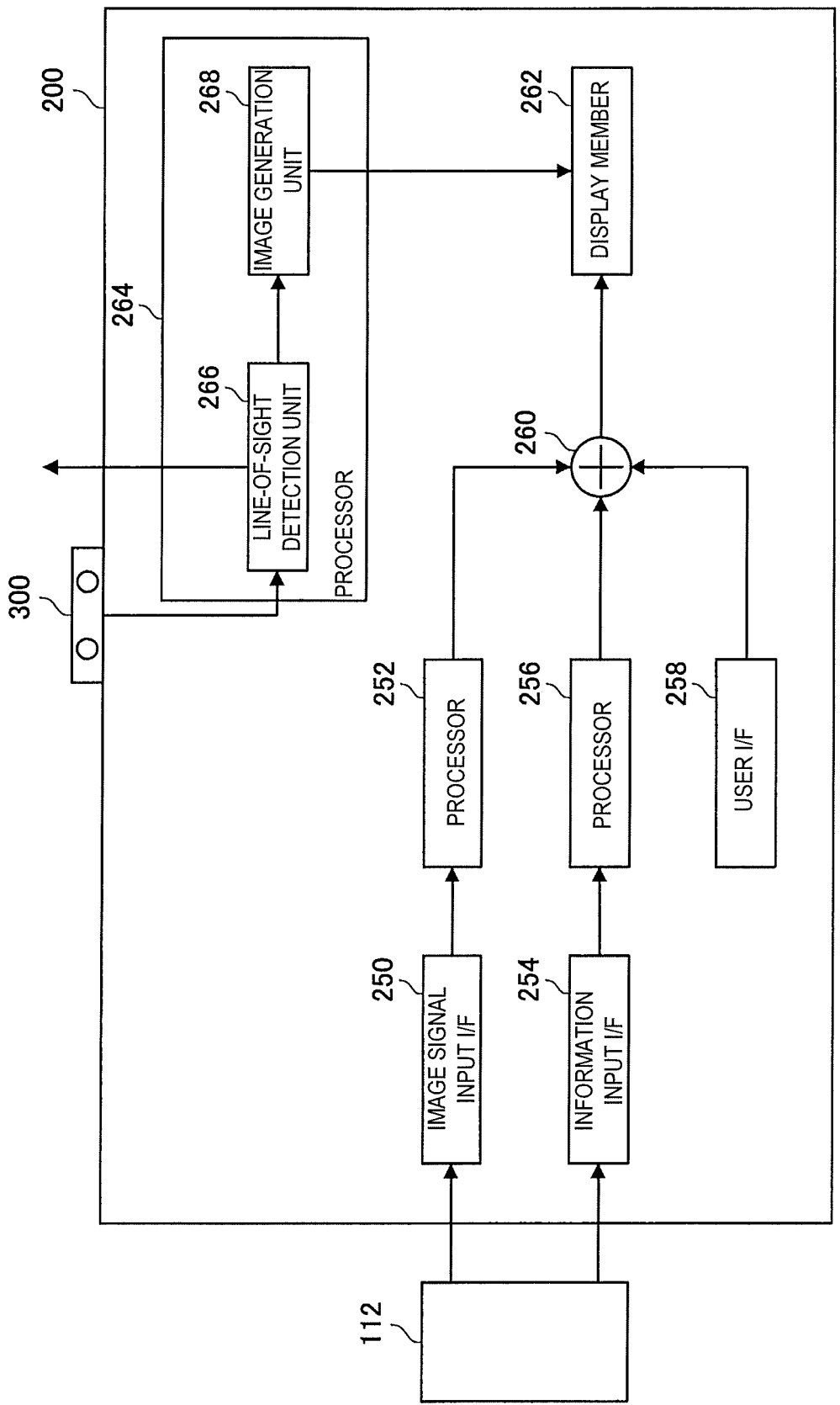
FIG. 9 is an explanatory diagram illustrating an example of a hardware configuration of a display device having both a function of detecting a line of sight and a function of causing the line of sight to be displayed on a display screen on the basis of the detection result of the line of sight.

FIG. 9 is an explanatory diagram illustrating an example of a hardware configuration of the display device 200 having both the function of detecting a line of sight and the function of causing the line of sight to be displayed on the display screen on the basis of the detection result of the line of sight. In FIG. 9, the control unit 112 illustrated in FIG. 1 and the line-of-sight detection sensor 300 serving as a sensor unit having a stereo camera are shown together.

The display device 200 has, for example, an image signal input interface 250, processors 252, 256, and 264, an information input interface 254, a user interface 258, a combiner 260, and a display member 262. In FIG. 9, the image signal input interface 250 is denoted by "image signal input I/F," the information input interface 254 is denoted by "information input I/F," and the user interface 258 is denoted by "user I/F."

The image signal input interface 250 is a communication interface to which signals are input, and the image signal input interface 250 receives image signals transmitted from the control unit 112 of the medical observation device 100. In addition, the image signal input interface 250 can receive display control signals along with image signals. An image signal received on the image signal input interface 250 is subject to arbitrary signal processing in the processor 252.

The information input interface 254 is another communication interface to which signals are input, and the information input interface 254 receives data indicating a state of an imaging function of the imaging device (e.g., data indicating a value indicating a zoom magnification, an F number, an EV, or a shutter speed value) transmitted from the control unit 112 of the medical observation device 100. The data indicating the state of the imaging function of the imaging device received by the information input interface 254 is subject to arbitrary data processing in the processor 256.

The user interface 258 is constituted by an operation device that can be operated by a user using the display device 200, and a combining method of the combiner 260 is switched through an operation on the user interface 258. As an operation device constituting the user interface 258, for example, a button, an arrow key, a rotary-type selector such as a jog dial, or a combination thereof is exemplified. In addition, in a case in which the display member 262 functions as a touch panel, the display member 262 and the user interface 258 may be integrated.

The combiner 260 selectively combines an image signal processed in the processor 252 and the data indicating the state of the imaging function of the imaging device processed in the processor 256. Combining or non-combining by the combiner 260 and a combining method are switched, for example, through an operation with respect to the user interface 258. In a case in which the combiner 260 does not perform combining, the combiner 260 outputs the image signal processed in the processor 252 to the display member 262.

The display member 262 is constituted by, for example, a display panel and various drivers, and displays an image corresponding to the transferred image signal on a display screen. In addition, on the display screen of the display member 262, one or both of the state of the imaging function of the imaging device and the position of the line of sight of the recognition target can be displayed.

The processor 264 has, for example, a line-of-sight detection unit 266 and an image generation unit 268, and plays a role of performing a line-of-sight detection process.

The line-of-sight detection unit 266 performs the line-of-sight detection process on a captured image acquired from the line-of-sight detection sensor 300 to detect a line of sight of a recognition target. The line-of-sight detection unit 266 transmits, for example, data indicating the detection result of the line of sight to the medical observation device 100. In addition, the line-of-sight detection unit 266 transfers the data indicating the detection result of the line of sight to the image generation unit 268.

The image generation unit 268 generates an image indicating a position of the line of sight of the recognition target (e.g., the circular image having the position of the line of sight denoted by reference sign O as the center in FIG. 6) on the basis of the data indicating the detection result of the line of sight transferred from the line-of-sight detection unit 266. Then, the image generation unit 268 transfers the generated image indicating the position of the line of sight of the recognition target to the display member 262, and thereby the position of the line of sight of the recognition target is displayed on the display screen of the display member 262.

With the hardware configuration illustrated in FIG. 9, for example, the display device 200 having both the function of detecting a line of sight and the function of displaying the line of sight on the display screen on the basis of the detection result of the line of sight is realized. Note that it is a matter of course that a hardware configuration of the display device 200 having both the function of detecting a line of sight and the function of displaying the line of sight on the display screen on the basis of the detection result of the line of sight is not limited to the example illustrated in FIG. 9.

[3] Example of Effects Exhibited By Using Medical Observation System According to Present Embodiment The following effects, for example, are exhibited by using the medical observation system according to the present embodiment. Note that it is a matter of course that an effect exhibited by using the medical observation system according to the present embodiment is not limited to the following examples.

- Brightness of a part (an example of a predetermined region) of a medical captured image including an operative site being observed by an operator can be optimized. Thus, even in a case in which an inside of an abdominal cavity of a patient with varying complex unevenness is imaged, a medical captured image with a higher S/N can be displayed on the display screen. In addition, the operator can concentrate on observing the medical captured image, and thus stress caused by surgery can be reduced.
- Since surgery (an example of medical practice) is performed on a predetermined region in which an operative site that an operator is observing is included, even if the display device has made progress in high resolution such as 4K or 8K, it rarely affects a size of the predetermined region. Thus, even if the display device makes progress in high resolution, the effect of reducing stress caused by the surgery is exhibited.
- By displaying a position of a line of sight of an operator on the display screen on which a medical captured image is being displayed, an intention of the operator can be shared with the surgery team.
- In a case in which a user interface image for controlling various apparatuses such as the medical observation device 100 is displayed on the display screen and a position of a line of sight of an operator is displayed on the display screen, the apparatuses can be controlled on the basis of the position of the line of sight of the operator.

(Program According to the Present Embodiment)

Usability can be improved by a processor and the like executing a program (e.g., a program that can execute the process relating to the control method according to the present embodiment) for causing a computer system to function as the medical observation device according to the present embodiment (or the control device according to the present embodiment) in the computer system. Here, as the computer system according to the present embodiment, a single computer or a plurality of computers are exemplified. A series of processes relating to the control method according to the present embodiment are performed by the computer system according to the present embodiment.

In addition, when the program for causing the computer system to function as the medical observation device according to the present embodiment (or the control device according to the present embodiment) is executed by the processor and the like in the computer system, an effect to be produced from display that is realized by the process relating to the above-descried control method according to the present embodiment can be exhibited.

It should be understood by those skilled in the art that various modifications, combinations, sub-combinations and alterations may occur depending on design requirements and other factors insofar as they are within the scope of the appended claims or the equivalents thereof.

Although it has been described above that, for example, the program (computer program) for causing the computer system to function as the medical observation device according to the present embodiment is provided, the present embodiment can also provide a recording medium in which the program is stored therealong.

The above-described configuration is an example of the present embodiment, and of course belongs to the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A medical observation device including:
an imaging control unit configured to control an imaging function of an imaging device,
in which the imaging control unit controls an exposure function of the imaging device on a basis of a detection result of a line of sight of a recognition target so that luminance of a predetermined region in a medical captured image obtained by the imaging device capturing an observation target is changed.

(2) The medical observation device according to (1), in which the imaging control unit controls the exposure function of the imaging device on a basis of a position of a line of sight of a recognition target specified from the detection result of the line of sight of the recognition target on a display screen on which the medical captured image is displayed so that the luminance of the predetermined region is changed.

(3) The medical observation device according to (2), in which the predetermined region is a region in which a position in the medical captured image corresponding to the position of the line of sight on the display screen is included.

(4) The medical observation device according to (3), in which the imaging control unit controls the exposure function so that luminance of a region other than the predetermined region in the medical captured image is decreased.

(5) The medical observation device according to (4), in which the imaging control unit controls a zoom function of the imaging device so that electronic zoom is performed on the predetermined region in conjunction with control of the exposure function.

(6) The medical observation device according to (3), in which the imaging control unit controls the exposure function so that diffused illumination light is radiated to a position of the observation target corresponding to the position in the medical captured image.

(7) The medical observation device according to (3), in which the imaging control unit controls the exposure function so that illuminance of the predetermined region in the medical captured image is increased.

(8) The medical observation device according to any one of (2) to (7), further including:
a display control unit configured to cause a position in the medical captured image corresponding to the position of the line of sight on the display screen to be displayed on the display screen on the basis of the detection result of the line of sight of the recognition target.

(9) The medical observation device according to (8), in which the display control unit causes the predetermined region in which the position in the medical captured image is included to be displayed on the display screen.

(10) The medical observation device according to (8) or (9), in which the display control unit further causes a user interface image for controlling the imaging function of the imaging device to be displayed on the display screen.

(11) The medical observation device according to any one of (8) to (10), in which the display control unit further causes a state of the imaging function of the imaging device to be displayed on the display screen.

(12) The medical observation device according to any one of (1) to (11), in which the imaging control unit controls the exposure function of the imaging device so that the luminance of the predetermined region is increased or luminance of the predetermined region is decreased.

(13) The medical observation device according to any one of (1) to (12), including:
the imaging device configured to be inserted into an inside of a body of a patient and image the inside of the body.

(14) The medical observation device according to any one of (1) to (12), including:
an arm including a plurality of links connected to each other by a joint; and
the imaging device supported by the arm.

(15) A medical observation system including:
a medical observation device including an imaging control unit configured to control an imaging function of an imaging device; and
a display device configured to display a medical captured image captured by the imaging device on a display screen,
in which the imaging control unit of the medical observation device controls the exposure function of the imaging device on a basis of a detection result of a line of sight of a recognition target so that luminance of a predetermined region in the medical captured image is changed.

What is claimed is:
1. A medical observation device comprising:
circuitry configured to
receive data regarding a line of sight of a recognition target, and
on a condition that the data indicates the line of sight of the recognition target has changed, control an exposure function of imaging device to change luminance of a predetermined region in a medical captured image obtained by the imaging device capturing an observation target.

2. The medical observation device according to claim 1, wherein the circuitry is configured to control the exposure function of the imaging device on a basis of a position of the line of sight of Flail the recognition target specified from the data regarding the line of sight of the recognition target on a display screen on which the medical captured image is displayed to change the luminance of the predetermined region.

3. The medical observation device according to claim 2, wherein the predetermined region is a region in which a position in the medical captured image corresponding to the position of the line of sight on the display screen is included.

4. The medical observation device according to claim 3, wherein the circuitry is configured to control the exposure function so that luminance of a region other than the predetermined region in the medical captured image is decreased.

5. The medical observation device according to claim 4, wherein the circuitry is configured to control a zoom function of the imaging device so that electronic zoom is performed on the predetermined region in conjunction with control of the exposure function.

6. The medical observation device according to claim 3, wherein the circuitry is configured to control the exposure function so that diffused illumination light obtained by diffusing illumination light is radiated to a position of the observation target corresponding to the position in the medical captured image.

7. The medical observation device according to claim 3, wherein the circuitry is configured to control the exposure function so that illuminance of the predetermined region in the medical captured image is increased.

8. A medical observation device comprising:
circuitry configured to
receive data regarding a line of sight of a recognition target,
control an exposure function of an imaging device on a basis of a position of the line of sight of the recognition target specified from the data regarding the line of sight of the recognition target on a display screen on which a medical captured image is displayed to change luminance of a predetermined region; and
cause a position in the medical captured image corresponding to the position of the line of sight on the display screen to be displayed on the display screen on the basis of the data regarding the line of sight of the recognition target.

9. The medical observation device according to claim 8, wherein circuitry is configured to cause the predetermined region in which the position in the medical captured image is included to be displayed on the display screen.

10. The medical observation device according to claim 8, wherein circuitry is configured to cause a user interface image for controlling an imaging function of the imaging device to be displayed on the display screen.

11. The medical observation device according to claim 8, wherein circuitry is configured to cause a state of an imaging function of the imaging device to be displayed on the display screen.

12. The medical observation device according to claim 1, wherein circuitry is configured to control the exposure function of the imaging device so that the luminance of the predetermined region is increased or luminance of the predetermined region is decreased.

13. The medical observation device according to claim 1, wherein the imaging device is to be inserted into an inside of a body of a patient and image the inside of the body.

14. The medical observation device according to claim 1, further comprising:
an arm including a plurality of links connected to each other by a joint
wherein the imaging device is supported by the arm.

15. A medical observation system comprising:
a medical observation device including an imaging device
circuitry configured to control an imaging function of the imaging device; and
a display to display a medical captured image captured by the imaging device on a display screen,
wherein the circuitry is configured to
receive data regarding a fine of sight of a recognition target, and
on a condition that the data indicates the line of sight of the recognition target has changed, control an exposure function of the imaging device to change luminance of a predetermined region in the medical captured image.

16. The medical observation system according to claim 15, wherein the circuitry is configured to control the exposure function of the imaging device on a basis of a position of the line of sight of the recognition target specified from the data regarding the line of sight of the recognition target on a display screen on which the medical captured image is displayed to change the luminance of the predetermined region.

17. The medical observation system according to claim 16, wherein the circuitry is configured to cause a position in the medical captured image corresponding to the position of the line of sight on the display screen to be displayed on the display screen on the basis of the data regarding the line of sight of the recognition target.

18. The medical observation system according to claim 17, wherein circuitry is configured to cause the predetermined region in which the position in the medical captured image is included to be displayed on the display screen.

19. The medical observation system according to claim 17, wherein circuitry is configured to cause a user interface image for controlling the imaging function of the imaging device to be displayed on the display screen.

20. The medical observation system according to claim 17, wherein circuitry is configured to cause a state of the imaging function of the imaging device to be displayed on the display screen.

\* \* \* \* \*